United States Patent
Wang et al.

(10) Patent No.: US 9,234,798 B2
(45) Date of Patent: Jan. 12, 2016

(54) SYSTEM AND METHOD FOR DETECTING NUMBER OF LAYERS OF A FEW-LAYER GRAPHENE

(71) Applicant: National Chung Cheng University, Chiayi County (TW)

(72) Inventors: Hsiang-Chen Wang, Chiayi County (TW); Guan-Huang Wu, Chiayi County (TW); Jhe-Ming Yang, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 319 days.

(21) Appl. No.: 13/923,587

(22) Filed: Jun. 21, 2013

(65) Prior Publication Data

US 2014/0376799 A1 Dec. 25, 2014

(51) Int. Cl.
| | |
|---|---|
| *G06K 9/00* | (2006.01) |
| *G01J 3/42* | (2006.01) |
| *H01L 21/66* | (2006.01) |
| *G01N 21/84* | (2006.01) |
| *G06T 7/00* | (2006.01) |
| *H04N 1/60* | (2006.01) |
| *G01B 11/06* | (2006.01) |
| *G06K 9/62* | (2006.01) |
| *G01J 3/44* | (2006.01) |
| *G01J 3/457* | (2006.01) |
| *G01N 21/31* | (2006.01) |
| *G01J 3/28* | (2006.01) |

(52) U.S. Cl.
CPC . *G01J 3/42* (2013.01); *G01B 11/06* (2013.01); *G01B 11/0625* (2013.01); *G01B 11/0633* (2013.01); *G01J 3/28* (2013.01); *G01J 3/44* (2013.01); *G01J 3/457* (2013.01); *G01N 21/31* (2013.01); *G01N 21/8422* (2013.01); *G06K 9/6267* (2013.01); *G06T 7/001* (2013.01); *G06T 7/0004* (2013.01); *H01L 22/10* (2013.01); *H01L 22/12* (2013.01); *H04N 1/6013* (2013.01); *G01J 2003/2826* (2013.01)

(58) Field of Classification Search
USPC ......... 382/100, 141, 152, 162, 165, 224, 312, 382/325
See application file for complete search history.

(56) References Cited

U.S. PATENT DOCUMENTS

| | | | | |
|---|---|---|---|---|
| 2011/0299720 | A1* | 12/2011 | Nolen et al. | 382/100 |
| 2012/0136601 | A1* | 5/2012 | Chen et al. | 702/81 |
| 2013/0087705 | A1* | 4/2013 | Hiura et al. | 250/307 |
| 2015/0103229 | A1* | 4/2015 | Nozawa | 348/342 |

OTHER PUBLICATIONS

Z. H. Ni, H. M. Wang, J. Kasim, H. M. Fan, T. Yu, Y. H. Wu, Y. P. Feng, and Z. X. Shen, "Graphene Thickness Determination Using Reflection and Contrast Spectroscopy", American Chemical Society, Nano Letters, vol. 7, No. 9, Jul. 2007, pp. 2758-2763.*

(Continued)

*Primary Examiner* — Eric Rush
(74) *Attorney, Agent, or Firm* — Fishman & Associates, LLC.

(57) ABSTRACT

Provided are a system and a method for detecting a number of layers of few-layer graphene employing multispectral image reproduction process to provide rapid detection of numbers of layers of few-layer graphenes on transparent or non-transparent substrates. The application of the system and method in relevant industries expedites validation and/or verification of the number of layers of an FLG product and improves the quality control efficiency thereof.

3 Claims, 24 Drawing Sheets

(56) References Cited

OTHER PUBLICATIONS

Inhwa Jung, Matthey Pelton, Richard Piner, Dmitriy A. Dikin, Sasha Stankovich, Supinda Watcharotone, Martina Hausner, and Rodney S. Ruoff, "Simple Approach for High-Contrast Optical Imaging and Characterization of Graphene-Based Sheets", American Chemical Society, Nano Letters, vol. 7, No. 12, 2007, pp. 3569-3572.*

Inhwa Jung, Jong-Soo Rhyee, Jong Yeog Son, Rodney S Ruoff, and Kyong-Yop Rhee, "Colors of graphene and graphene-oxide multilayers on various substrates", Nanotechnology, vol. 23, No. 2, Jan. 2012, pp. 1-8.*

H.C. Neto, F. Guinea, N.M.R. Peres, K.S. Novoselov, A.K. Geim: The electronic properties of graphene. Reviews of Modern Physics, 81, 109-162 (2009).

K.S. Kim, Y.Z. Houk Jang, S.Y. Lee, J.M. Kim, K.S. Kim, J.H. A.P. Kim, J.Y. Choi, B.H. Hong: Large-scale pattern growth of graphene films for stretchable transparent electrodes. Nature, 457, 706-710 (2009).

D.L., Marc B. M.L. Scott Gilje, R. B. Kaner, G.G. Wallace: Processable aqueous dispersions of graphene nanosheets. Nature Nanotechnology, 3, 101-105 (2008).

Z.N. Ying, W.T. Yu, Z. Shen: Raman Spectroscopy and Imaging of Graphene. Nano Res 1, 273-291 (2008).

N. Mohanty, D. Moore, Z. Xu, T.S. Sreeprasad, A. Nagaraja, A.A. Rodriguez, V. Berry: Nanotomybased production of transferable and dispersible graphene nanostructures of controlled shape and size. Nature communications, 3, article No. 844 (2012).

Maher F. El-Kady et al.: Laser Scribing of High-Performance and Flexible Graphene-Based Electrochemical Capacitors. Science 335 (6074), 1326-1330 (2012).

Jae Hun Seol et al.: Two-Dimensional Phonon Transport in Supported Graphene. Science, 328 (5975), 213-216 (2010).

H. Yang, et al.: Graphene Barristor, a Triode Device with a Gate-Controlled Schottky Barrier. Science, 336 (6085), 1140-1143 (2012).

Y.W., H.W. Tong, X.F. Xu, B. Ozyilmaz, K.P. Loh: Interface Engineering of Layer-by-Layer Stacked Graphene Anodes for High-Performance Organic Solar Cells. Adv. Mater. 23 (13), 1514-1518 (2011).

W.Z., C.T. Lin, K.K. Liu, T. Tite, C.Y. Su, C.H. Chang, Y.H. Lee, C.W. Chu, K.H. Wei, J.L. Kuo, L.J. Li: Opening an Electrical Band Gap of Bilayer Graphene with Molecular Doping. ACS Nano, vol. 5, No. 9, 7517-7524 (2011).

S. Lee, K. Lee, C.H. Liu, Z. Zhong: Homogeneous bilayer graphene film based flexible transparent conductor. Nanoscale, 4, 639-644 (2012). DOI: 10.1039/c1nr11574j (2011).

P. Blake, E.W. Hill, A.H. Castro Neto, K.S. Novoselov, D. Jiang et al.: Making graphene visible, Appl. Phys. Lett., 91, 063124 (2007).

I.J. Matthew Pelton, R.P. Dmitriy A. Dikin, S.S. Ovich, S.W. Rotone, M. Hausner, R.S. Ruoff: Simple Approach for High-Contrast Optical Imaging and Characterization of Graphene-Based Sheets, Nano Letters, 7 (12), 3569-3575 (2007).

L. Gao, W. Ren, F. Li, H.M. Cheng: Total Color Difference for Rapid and Accurate Identification of Graphene, ACS Nano 2 (8), 1625-1633 (2008).

Y.Y. Wang, Z.H. Ni, T. Yu, Z.X. Shen, H.M. Wang, Y.H. Wu, W. Chen, A.T. Shen: Raman Studies of Monolayer Graphene: the Substrate Effect, J. Phys. Chem. 10637-10640 (2008).

I.J., J.S. Rhyee, J.Y. Son, R.S. Ruoff, K.Y. Rhee: Colors of graphene and graphene-oxide multilayers on various substrates. Nanotechnology, 23, 025708 (2012).

Z.H. Ni, H.M. Wang, J. Kasim, H.M Fan, T. Yu, Y.H. Wu, Y.P. Feng, Z.X. Shen: Graphene Thickness Determination Using Reflection and Contrast Spectroscopy. Nano Lett., 7 (9), 2758-2763 (2007).

Y.W. Zhu, S. Murali, W. Cai, X. Li, Ji Won Suk, J.R. Potts, R.S. Ruoff: Graphene and Graphene Oxide: Synthesis, Properties, and Applications. Adv. Mater., 22 (35), 3906-3924 (2010).

Y.K. Koh, M.H. Bae, D.G. Cahill, N.E. Pop: Reliably Counting Atomic Planes of Few-Layer Graphene (n>4). ACS Nano, 5 (1), 269-274 (2011).

W. Liu, H. Li, C. Xu, Y. Khatami, K. Banerjee: Synthesis of high-quality monolayer and bilayer graphene on copper using chemical vapor deposition, Carbon, 49 (13), 4122-4130 (2011).

J.S. Park, A. Renia, R. Saito, J. Kong, G. Dresselhaus, M.S. Dresselhaus: G band Raman spectra of single, double and triple layer graphene, Carbon, 47 (5), 1303-1310 (2009).

M.S. Dresselhaus, G. Dresselhaus, R. Saito, A. Jorio: Raman spectroscopy of carbon nanotubes, Physics Reports, 409 (2), 47-99 (2005).

A.C. Ferrari, J.C. Meyer, V. Scardaci, Casiraghi, M. Lazzeri, F. Mauri, S. Piscanec, D. Jiang, K.S. Novoselov, S. Roth, A.K. Geim: Raman Spectrum of Graphene and Graphene Layers, Physical Review Letters, 97, 187401 (2006).

* cited by examiner

SYSTEM AND METHOD FOR DETECTING NUMBER OF LAYERS OF A FEW-LAYER GRAPHENE

BACKGROUND OF THE INVENTION

1. Field of the Invention

The present invention relates to a system for detecting the number of layers of a few-layer graphene, especially to a system with an image analysis and processing means. The present invention also relates to a method for detecting the number of layers of a few-layer graphene, especially to a method using an image analysis and processing means.

2. Description of the Prior Art

The visualization of graphene is regarded as an issue of increasing importance to the developing graphite technology, especially regarding confirming the number ("N") of layers of a few-layer graphene (hereinafter "FLG"). Conventional techniques for distinguishing number of layers of FLG include: Raman spectroscopy, transmission spectroscopy, atomic force microscopy (hereinafter "AFM") and optical microscopy.

A. Raman Spectroscopy and Transmission Spectroscopy

As described in reference 17, Raman spectroscopy allows detection of number of layers of an FLG by changes in G-band Raman intensity and differences in 2D-band.

Reference 19 further describes an application of Raman spectroscopy on a silica/silicon ($SiO_2$/Si) substrate for counting the number of atomic layers of an FLG. The counting via Raman spectroscopy of the number of atomic layers of the FLG on a silica/silicon substrate is accomplished by examining the sum of intensities of phonon peaks for graphene and silicon so as to obtain information for the number of the layers of the FLG, even if the number of layers is larger than four (N>4).

It is also revealed in reference 18 that the transmittance of a single-layer graphene is 97.7%, which indicates that information for the number of the layers of an FLG may be obtained by examining the transmittance of the FLG.

Validation of the information obtained with the aforementioned techniques based on Raman spectroscopy or transmission spectroscopy, however, requires verifications that are significantly time-consuming and labor-intensive. For example, it requires three hours to verify and accomplish a task for examining an FLG having an area of 50 $\mu m^2$. In addition, the technique based on Raman spectroscopy bears certain vague zones within which the number of layers of an FLG cannot be determined.

B. Atomic Force Microscopy

In accordance with reference 19, the thickness of a single-layer graphene is 0.34 nm. A technique based on AFM detects the roughness of the surface of an FLG and thereby obtains information of the number of layers of the FLG. It is to be noted that such a technique based on AFM also requires a significant amount of time to complete a measurement.

C. Optical Microscopy

A technique based on optical microscopy, such as one described in reference 14, may be employed to more thoroughly analyze the color of an FLG on a dielectric layer or substrate made of silica, silicon, silicon nitride or aluminum oxide, so as to distinguish different thin-film-optical characteristics of FLGs having different numbers of layers.

The technique reference 12 relates to a method for examining number of layers of an FLG on specific substrates via microscopic imaging skills. Reference 12 has found that it is possible and feasible to detect the number of layers of an FLG on a 300 nm layer of silicon, whereby the silicon layer is formed on a silica substrate. Furthermore, an FLG on a 100 nm layer of silicon is most visualizable in terms of determining the number of layers of the FLG. Reference 12 also indicates that a silica/silicon substrate with a 285 nm oxide layer significantly increases the visualizability of an FLG thereon, the rationale of which has been verified by color difference calculations.

Reference 13 has discussed a multispectral optical microscopic method for distinguishing and measuring effective optical characteristics of a graphite of nanometer-level thickness as a basal material. Such basal material is formed on a silicon substrate on a thin insulation layer. Selecting suitable optical characteristics and a dielectric layer of proper thickness allows revealing of the contrast of an FLG and the substrate. The effective refractive index and optical absorption coefficient of a graphene oxide, thermally reduced graphene oxide as well as FLG are obtained by comparing the estimated and measured differences thereof.

Reference 15 has demonstrated that the measurement for number of layers of FLGs on different substrates made of silicon carbide, silica/silicon, quartz, silicon and glass are subject to the different lattice constants and the electronic structures. Reference 15 has also indicated that an FLG on a substrate of quartz or silica/silicon demonstrates higher contrast of color difference.

Reference 14 has disclosed a conventional technology using light sources of different wavelength ranges for color difference simulation of FLGs on silica/silicon substrate, silicon nitride substrate and aluminum oxide substrate. The conventional technology of reference 14 has taught that the silicon nitride substrate is a suitable substrate for an FLG to be identified, while the silica/silicon substrate and the aluminum oxide substrate are suitable for graphene thin films of average and high number of layers.

Reference 16 is related to a color difference analyzing method performed on FLGs deposited on silica/silicon and silica/air substrates. Reference 16 has described the colors of FLGs and graphene-oxides deposited on different dielectric layers. Reference 16 has also presented analyses of thicknesses of materials, types of dielectric layers, and existence of back silicon substrates. It has been indicated that the graphene-oxide layer periodically alters its color with the increase of the thickness of the material. The graphene layer on the same substrate, however, has demonstrated saturated and constant color without periodical alternation.

As the foregoing literatures have suggested, conventional technologies may employ optical microscopy, especially multispectral optical microscopy, to expedite imaging so as to provide a rapid and intuitive method for detecting number of layers of FLG. The conventional technologies employing optical microscopy, however, are not applicable without substrates of specific thicknesses. It is also to be noted that, these conventional technologies are not feasible with transparent substrates.

Furthermore, conventional technologies that employ optical microscopy to examine number of layers of FLGs are indeed capable of visually recognizing the number of layers through microscopic means. For example, the number of layers of an FLG deposited on a 300-nm silica dielectric layer of a silicon substrate may be detected using the aforementioned conventional means. In order to make the conventional optical microscopic technologies feasible, it is, however, necessary to make the FLG with a method having increased steps and manufacture processes.

The conventional optical microscopic technologies fail to visualize distinguishable contrast for examining numbers of layers of FLGs. For example, the contrast obtainable when observing a 5-layer FLG printed on a glass substrate with conventional optical microscopic means is barely visible for examining the number of layers of an FLG.

To overcome the shortcomings, the present invention provides a system and a method for the detection of the number of graphene layers to mitigate or obviate the aforementioned problems, such as the time-consuming and labor-intensive verifications for the techniques based on Raman spectroscopy or transmission spectroscopy, the expensive instruments and time-consuming measurements of the technique based on AFM, and the restrictions on substrate thickness and transparency and the lack of visible contrast of the conventional technologies based on optical microscopy.

SUMMARY OF THE INVENTION

The main objective of the present invention is to provide a system for the detection of the number of graphene layers. Another aspect of the present invention is to provide a method for the detection of the number of graphene layers.

The system in accordance with the present invention has a visualization module, an acquisition module and a reproduction module. The visualization module holds and illuminates an FLG sample. The acquisition module performs an optical observation on the FLG sample. The reproduction module is operably connected to the acquisition module to provide information of detection of a number of layers of the FLG for reproducing a multispectral color image.

The method in accordance with the present invention has a spectral database construction process and a multispectral image reproduction process.

The spectral database construction process has a spectra-analyzing step, a principal component analysis (hereinafter "PCA") step, and a database constructing step. In the spectra-analyzing step, spectral analyses are performed for FLGs of different numbers of layers on different substrates, based on which resulting information is obtained. In the PCA step, PCA is performed with the resulting information to obtain a distinguishing formula. In the database constructing step, a database is built based on the resulting information of the spectral analyses and the distinguishing formula to present a relationship between a number of layers of an FLG and the distinguishing formula.

The multispectral image reproduction process has an acquisition step, an analyzing step, a categorizing step, an enhancing step, a reproducing step, and an examining step. In the acquisition step, an image of an FLG is acquired. In the analyzing step, the image is analyzed to obtain a transmission spectrum of the FLG. In the categorizing step, the transmission spectrum is categorized according to the aforementioned database constructed via spectral analysis and PCA so as to obtain a categorization result. In the enhancing step, a simulation spectrum is determined based on the categorization result. In the reproducing step, a color image is reproduced with the simulation spectrum. In the examining step, a number of layers of the FLG is determined by examining the color image.

The system and the method in accordance with the present invention employ multispectral image reproduction process implemented with means such as optical microscopes and charge-coupled devices (hereinafter "CCD") to provide rapid detection of numbers of layers of FLGs on transparent or non-transparent substrates. The application of the present invention in relevant industries expedites validation and/or verification of the number of layers of an FLG product and improves the quality control efficiency thereof.

The present invention utilizes colorimetric means such as multispectral imaging based on spectra demonstrated owing to inter-layer destructive interference or inter-layer constructive interference. With PCA and quantification of spectral information, optical microscopic images of FLGs having different numbers of layers may be categorized into groups defined by the proportionality coefficient of a first PCA and a second PCA, so as to provide a system and a method for analyzing numbers of layers of FLGs.

Specifically, the present invention employs multispectral imaging techniques combining PCA for threshold determination and obtains reproduced images of FLGs having different numbers of layers, in order to rapidly detect a number of layers of an FLG.

As a result, the present invention mitigates or obviates the problems of the prior art and has overcome the restrictions of substrate thickness and structure. The present invention is capable of readily and correctively detecting numbers of layers of FLGs. Furthermore, the present invention employs multispectral optical microscopy, PCA, color corresponding conversion and linear regression to reproduce color for an FLG image without adjusting color alternation owing to illumination of microscopic imaging means. The straightforward and simple algorithms and the structure of the apparatuses for the method and system in accordance with the present invention have effectively implemented detection and analysis for FLGs, thereby saving the time and intense labor for the conventional technologies without relying on time-consuming measurements using expensive instruments such as AFM. In other words, the present invention indeed provides an effective, low-cost and time-saving technique to conveniently detect numbers of layers of FLGs.

Other objectives, advantages and novel features of the invention will become more apparent from the following detailed description when taken in conjunction with the accompanying drawings.

DETAILED DESCRIPTION OF THE PREFERRED EMBODIMENTS

A. System for Detecting the Number of Layers of FLG

Figure 1:
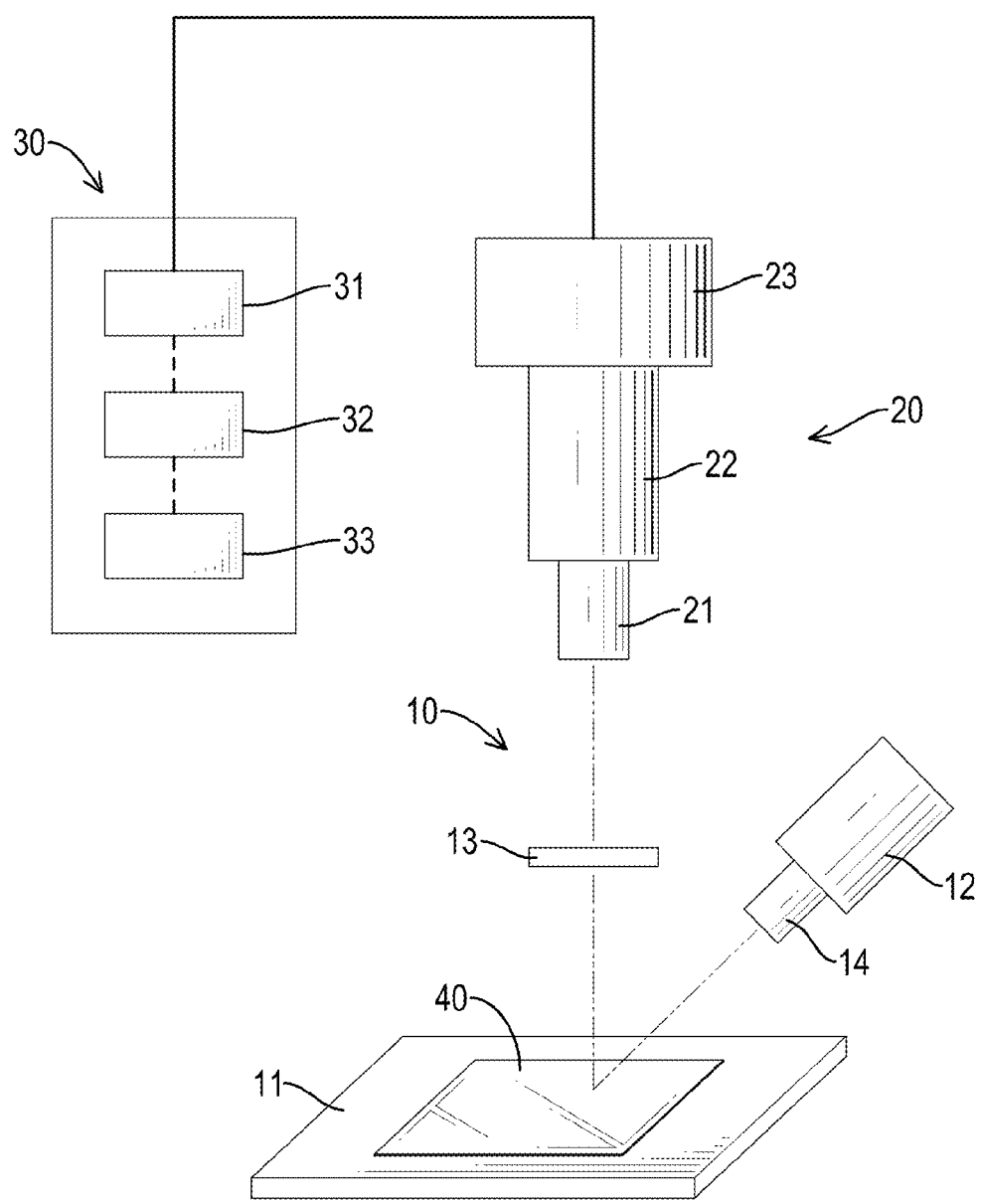
FIG. 1 is a schematic diagram of a system in accordance with the present invention.

With reference to FIG. 1, the system in accordance with the present invention comprises a visualization module 10, an acquisition module 20 and a multispectral imaging reproduction module 30.

The visualization module 10 holds an FLG sample 40 and illuminates the FLG sample 40 with a light source by projecting a light allowing the FLG sample 40 to be optically observed. Specifically, the visualization module 10 comprises a platform member 11 and an illumination member 12. Preferably, the visualization module 10 further comprises a magnification member 13, which comprises a structure for magnifying an image of the FLG sample 40 held by the platform member 11 and providing an enlarged image thereof.

The platform member 11 is for holding the FLG sample 40. The illumination member 12 provides a light source from which a light is projected to the FLG sample 40 held by the platform member 11. The magnification member 13 is mounted to the platform member 11 so as to magnify an image of the FLG sample 40 held.

The visualization module 10 further comprises an optional filter member 14. The filter member 14 is positioned in a light projecting path from the illumination member 12. The filter member 14 filters a light from the illumination member 12 in order to provide a filtered light of a band suitable for detecting the FLG sample 40 held by the platform member 11. The filter member 14 comprises filters, which include red, green, blue, cyan, magenta and yellow filters, to be used alternately or in combination. In addition, in absence of the optional filter member 14, the illumination member 12 may be an illuminating means capable of using switchable light sources to provide lights of different colors, or lights of different bands.

Figure 2:
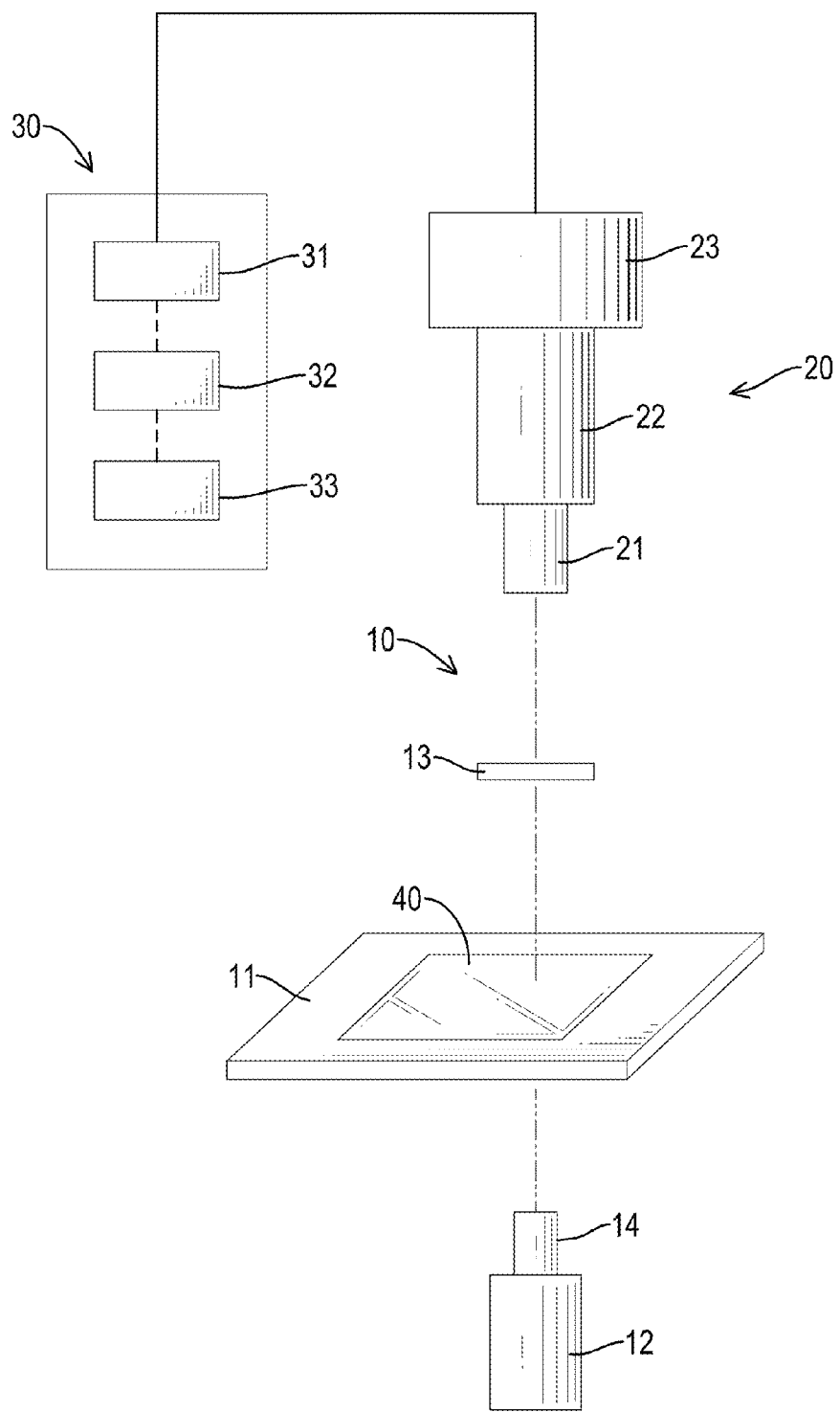
FIG. 2 is another schematic diagram of the system in FIG. 1.

With reference to FIG. 2, the illumination member 12 of the visualization module 10, other than comprising a reflective structure to reflectively project lights to the FLG sample 40 as having been shown in FIG. 1, may comprise a beaming structure that operates with a transparent platform member 11 for directly providing lights through the transparent platform member 11 to the FLG sample 40 for observation. Preferably, the illumination member 12 comprises a reflective structure as shown in FIG. 1 and a beaming structure as shown in FIG. 2 and is capable of switching the reflective structure and beaming structure. In other words, the illumination member 12 may comprise a reflective structure which projects a light reflectively to the platform member 11, a beaming structure which directly provides lights through a transparent platform member 11, or a switchable structure which comprises both the reflective structure and the beaming structure and is capable of switching the structures.

The acquisition module 20 comprises a structure for performing an optical observation of the FLG sample 40. Specifically, the acquisition module 20 is positioned in an output path of the visualization module 10 in which the FLG sample 40 is optically observed, and comprises a CCD member 22, a lens member 21 and a capturing member 23.

The CCD member 22 comprises an array formed with rows and columns of photosensitive units for respectively recording digital signals as pixel information of an electronic image. The CCD member 22 receives an image of the FLG sample 40 of the platform member 11 which has been magnified by the magnification member 13.

The lens member 21 is operably connected to the CCD member 22 for focusing the magnified image at the CCD member 22. Preferably, the lens member 21 focuses a light from the illumination member 12 through the FLG sample 40 at the CCD member 22.

The capturing member 23 is an image capturing means operably connected to the CCD member 22 for acquiring information of the magnified image focused by the lens member 21, which may be a camera or a spectrometer. More preferably, the spectrometer is a spectrometer of model number CS1000A of Konica Minolta or a spectrometer of model number QE65000 of Ocean Optics.

The reproduction module 30 is operably connected to the acquisition module 20 to provide information of detection of a number of layers of the FLG sample 40. The reproduction module 30 receives information from the capturing member 23 for the magnified image of the FLG sample 40 and comprises an implementation for a spectral analyzing step 31, an enhancing step 32 for color image categorizing, and a reproducing step 33, so as to process and to display the magnified image of the FLG sample 40 for a user to intuitively and rapidly examine a number of layers of the FLG sample 40.

B. Method for Detecting the Number of Layers of FLG

The method in accordance with the present invention comprises a spectral database construction process and a multispectral image reproduction process, wherein the spectral database construction process builds a database of numbers of layers of FLGs, based on which a detection by a reproduced multispectral color image for a number of layers of an FLG is performed in the multispectral image reproduction process.

1. The database construction process comprises a spectra-analyzing step, a PCA step and a database constructing step.

(1) In the spectra-analyzing step, spectral analyses are performed for FLGs of different numbers of layers on different substrates, based on which resulting information is obtained. Specifically, the spectra-analyzing step comprises the following procedures:

(1-a) Preparing FLGs formed on different substrates, for example, developing FLGs on silica/silicon substrates or glass substrates;

(1-b) Obtaining images of the FLGs, for example, capturing images of the FLGs via an acquisition means such as a microscope and a camera;

(1-c) Confirming the numbers of layers of the FLGs, for example, via Raman spectroscopy, transmission spectroscopy, or AFM; and (1-d) Performing spectral analyses of the transmission spectra of the FLGs and providing resulting information thereof.

(2) In the PCA step, PCA is performed with the resulting information to obtain a distinguishing formula. Specifically, the PCA step comprises the following procedures:

(2-a) Performing PCA for the FLGs of different numbers of layers on different substrates and obtaining a PCA result thereof; and (2-b) Based on the PCA result, a distinguishing formula as shown in the following Table 1 is determined for FLGs having different numbers of layers on different substrates, provided that y0 is the first principal component and y1 is the second principal component.

TABLE 1

| number of layers of FLG | formula |
|---|---|
| 1 | $-1.9348 < y0 < -1.2234$ |
|   | $-0.0047 < y1 < 0.0292$ |
| 2 | $-1.1640 < y0 < -0.2308$ |
|   | $0.0134 < y1 < 0.0420$ |
| 3 | $-0.2308 < y0 < 0.4213$ |
|   | $0.0279 < y1 < 0.0560$ |
| 4 | $0.4952 < y0 < 1.6962$ |
|   | $0.0175 < y1 < 0.0584$ |
| 5 | $1.6962 < y0 < 2.4659$ |
|   | $-0.0415 < y1 < 0.0175$ |
|   | $-0.0415 < y1 < 0.0175$ |

(3) In the database constructing step, a database is built based on the resulting information of the spectral analyses and the distinguishing formula to present a relationship between a number of layers of an FLG and the distinguishing formula.

2. The multispectral image reproduction process comprises an acquisition step, an analyzing step, a categorizing step, an enhancing step, a reproducing step, and an examining step.

(1) In the acquisition step, an image of an FLG, of which a number of layers is to be detected, is acquired via an acquisition means such as a microscope and a camera.

(2) In the analyzing step, the image is analyzed to obtain a transmission spectrum of the FLG.

(3) In the categorizing step, the transmission spectrum is categorized according to the aforementioned database constructed via spectral analysis and PCA so as to obtain a categorization result.

(4) In the enhancing step, a simulation spectrum is determined based on the categorization result.

(5) In the reproducing step, a color image is reproduced with the simulation spectrum.

(6) In the examining step, a number of layers of the FLG is determined by examining the reproduced color image which makes possible an intuitive and rapid examination process.

Preferably, the method for detecting numbers of layers of FLGs is implemented in the reproduction module 30. The reproduction module 30 applies the information received from the capturing member 23 of the magnified image of the FLG sample 40 to perform the aforementioned acquisition step for acquiring an image of the FLG sample. After analyzing the image in the analyzing step 31, a categorization result is obtained in the categorizing step, so as to further enhance and reproduce the magnified image of the FLG sample 40 in the enhancing step 32 and reproducing step 33, in order to provide a user with a reproduced and enhanced image to perform the examining step for detecting a number of layers of the FLG sample 40.

Figure 3:
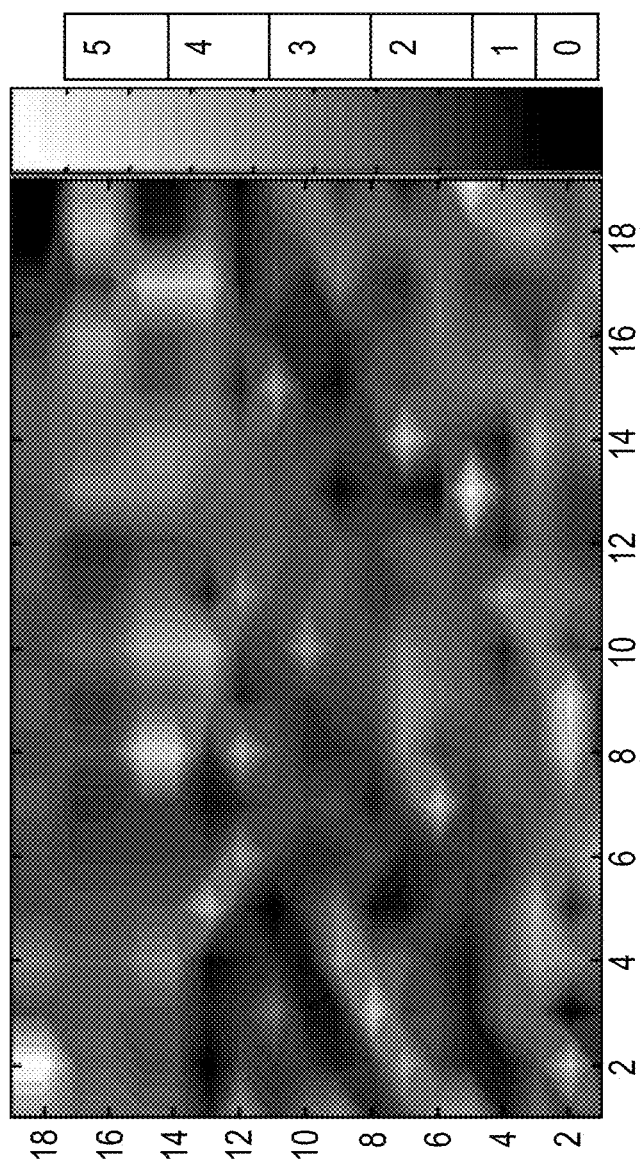
FIG. 3 is a grayscale image of an FLG on a glass substrate obtained using Raman spectroscopy analysis, whereby grayscales corresponding to numbers of layers of the FLG are marked with numerical symbols 0 to 5.

Take a 5-layer FLG on a glass substrate for example, in the case that the FLG in question is analyzed with Raman spectroscopy, a time-consuming and labor-intensive analyzing process would be unavoidable, which makes impossible an intuitive and rapid determination of the number of layers of the FLG. With reference to FIG. 3, there are considerably vague zones in the results obtained with technique based on Raman spectroscopy, within which the number of layers of the FLG is difficult to be determined.

Conversely, the system and the method in accordance with the present invention rapidly distinguishes transmission spectra of FLGs and employs color image reproduction to expedite detecting processes for numbers of layers of FLGs, which significantly obviates the shortcomings of the conventional techniques of the prior art.

C. Examples

Example 1

The instant example relates to preparation of an FLG.

In the instant example, a copper foil is employed as a catalyst for developing large-area single-layer graphene thin films under a low pressure environment, using methane as a carbon source. Developed graphene thin films are then transferred with polymethylmethacrylate (PMMA) to substrates of various types, such as silica/silicon substrates or glass substrates. Details for preparing the FLG are within the scope of the prior art and thus are omitted here.

Figure 5:
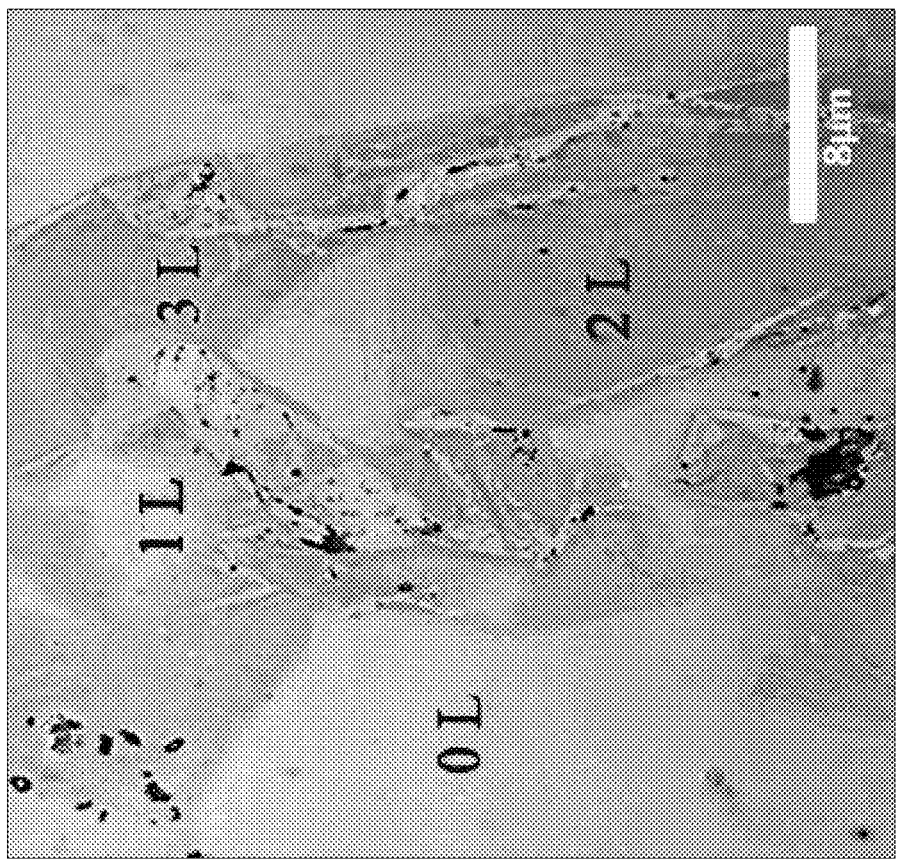
FIG. 5 is an image of a 3-layer FLG on a silica/silicon substrate.

With reference to FIG. 5, a 3-layer FLG is formed on a silica/silicon substrate. On the silica/silicon substrate there are zero-layer (marked with the symbol "0L") regions, that is, bare substrate without being covered by graphene, and one-layer (marked with the symbol "1L"), two-layer (marked with the symbol "2L") and three-layer (marked with the symbol "3L") regions covered respectively by corresponding layers of graphene.

Figure 6:
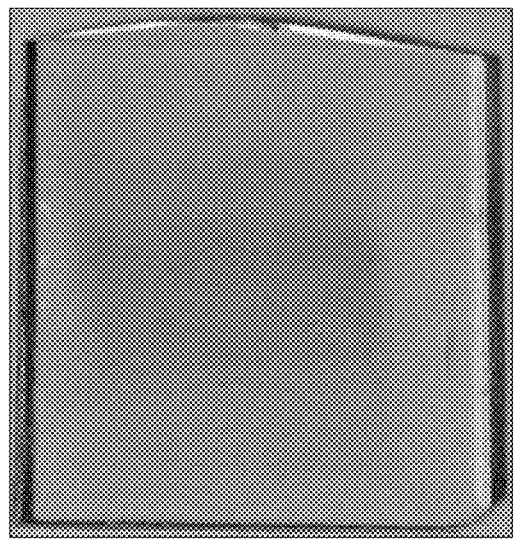
FIG. 6 is a top view of a 5-layer FLG on a glass substrate.
Figure 7:
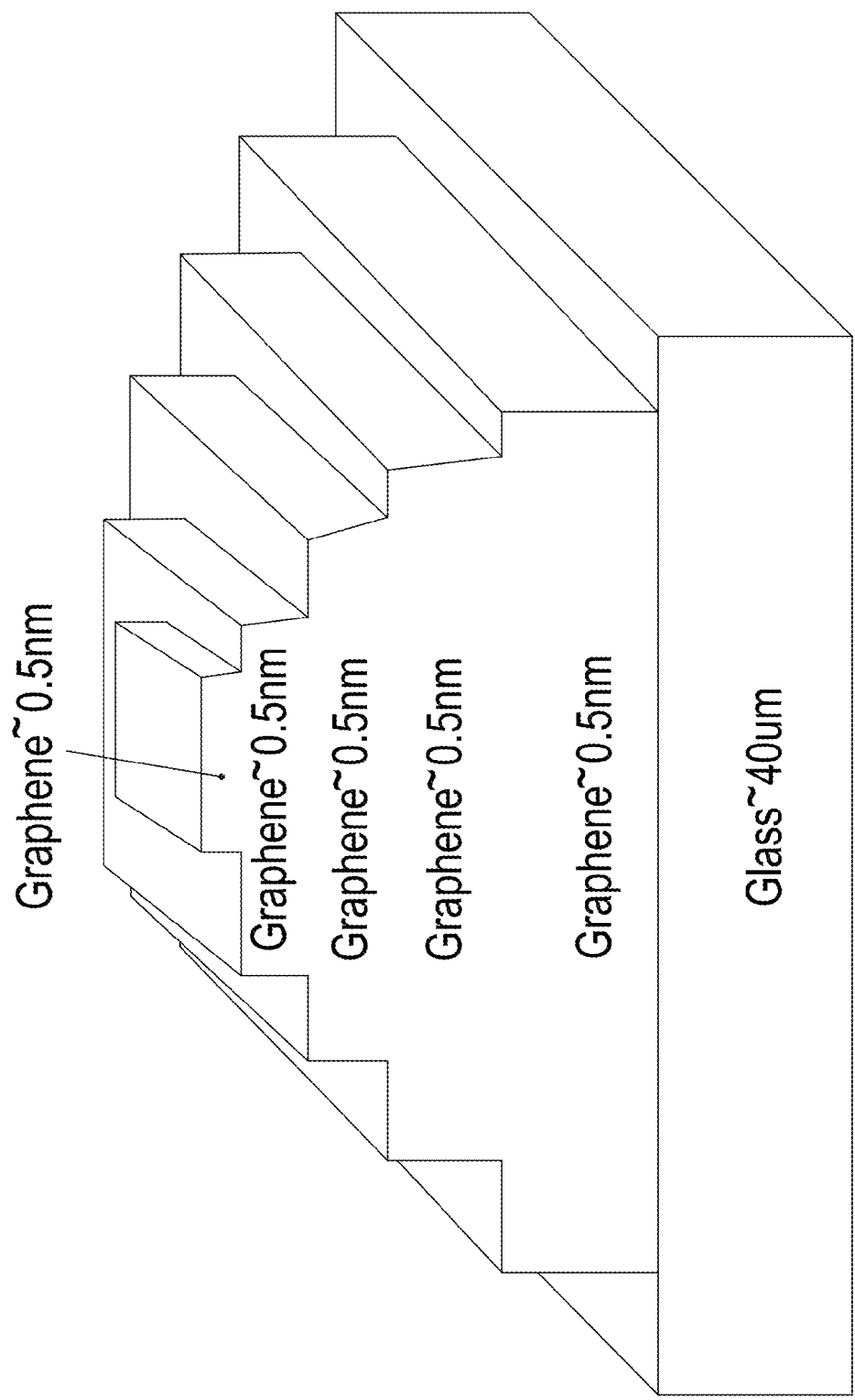
FIG. 7 is a schematic diagram of the FLG in FIG. 6.
Figure 9:
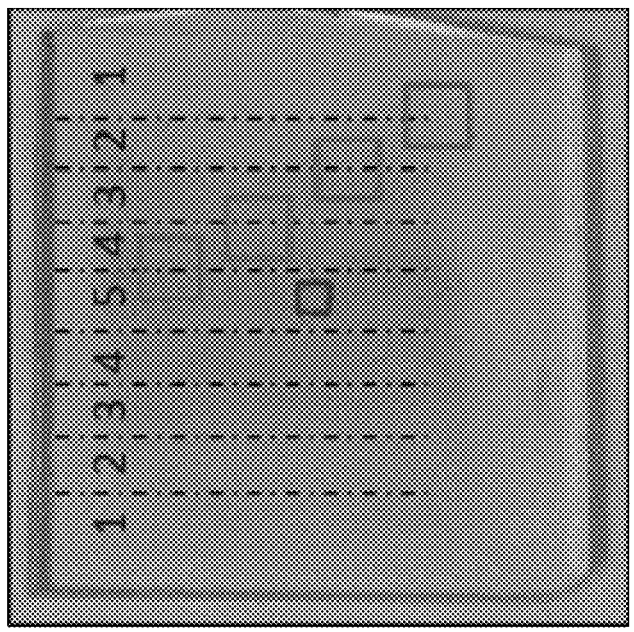
FIG. 9 is an image of the FLG in FIG. 6, whereby ribbon regions of different numbers of layers are marked with dash lines and symbols 1 LG to 5 LG (1-layer graphene to 5-layer graphene.) One square area within the 5 LG ribbon region is marked out, and so are four square areas respectively covering two ribbon regions of different layers.
Figure 8:
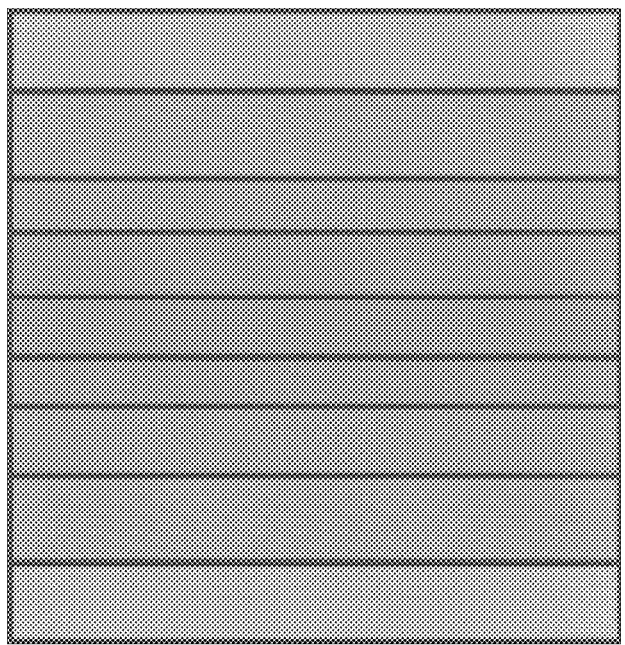
FIG. 8 is a schematic top view of the FLG in FIG. 6.
Figure 11:
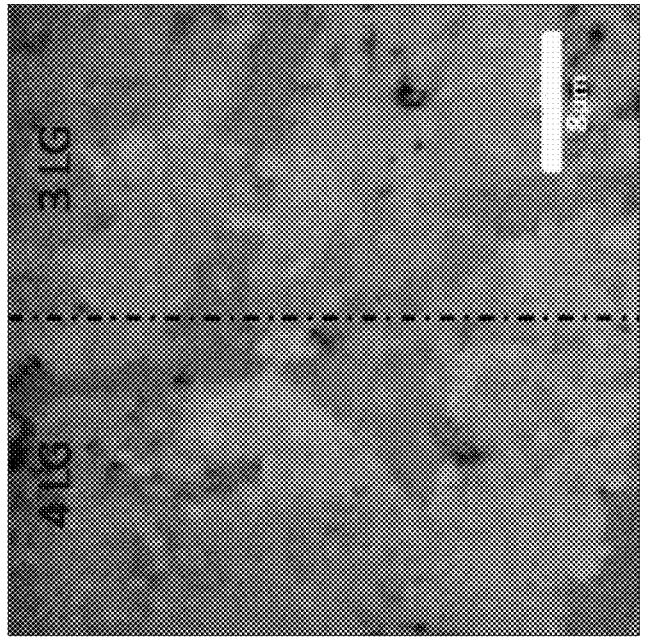
FIG. 11 is an image of the square area marked out in FIG. 9 covering the 4 LG and 3 LG ribbons.
Figure 10:
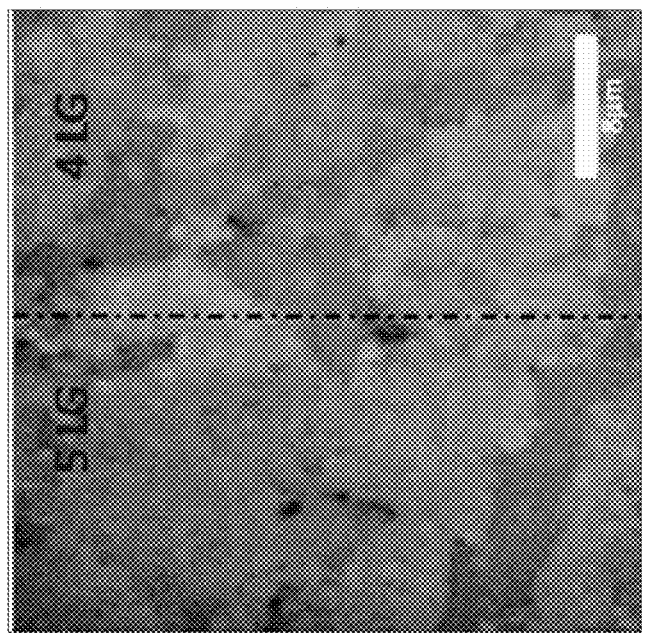
FIG. 10 is an image of the square area marked out in FIG. 9 covering the 5 LG and 4 LG ribbons.
Figure 13:
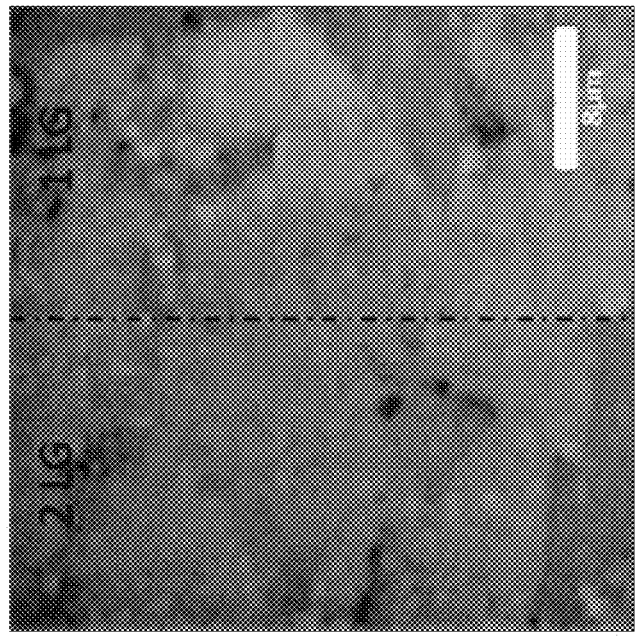
FIG. 13 is an image of the square area marked out in FIG. 9 covering the 2 LG and 1 LG ribbons.
Figure 12:
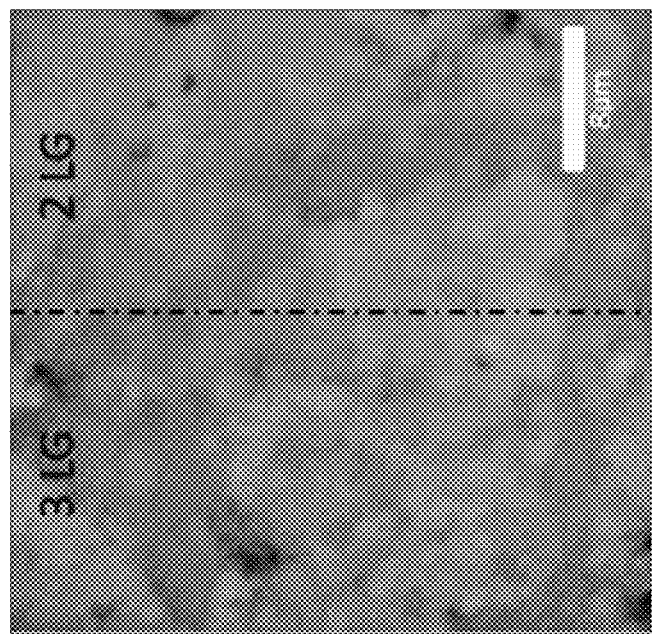
FIG. 12 is an image of the square area marked out in FIG. 9 covering the 3 LG and 2 LG ribbons.
Figure 14:
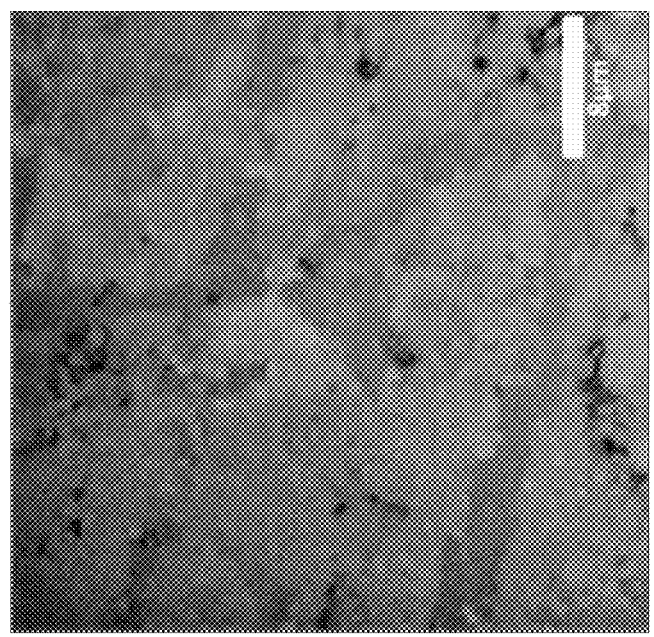
FIG. 14 is an image of the square area marked out in FIG. 9 within the 5 LG ribbon.

With reference to FIG. 6, a 5-layer FLG formed on a glass substrate is extremely difficult to be directly observed with an optical microscope in terms of distinguishing numbers of layers of the FLG on the substrate. As shown in FIG. 7, in the instant example, the numbers of layers decrease from a center ribbon region to lateral regions. The ribbon regions are partitioned as shown in FIG. 8 and areas as demonstrated in FIG. 9 and FIGS. 10 to 14 are selected for analyses.

Example 2

The instant example relates to a matrix of transformation between a spectrometer and an image-acquiring device. The image-acquiring device employed in the instant example comprises an optical microscope and a CCD camera operably connected to the microscope.

The spectrometer employed in the instant example is model number QE65000 spectrometer of Ocean Optics. The spectrometer is used to obtain transmission spectra of the 24 colors listed in Macbeth ColorChecker within the visible band of spectrum.

A model is built by multispectral calculation based on the obtained transmission spectra of the 24 colors. The color differences between simulated colors and the image-acquiring device are shown in Table 2, which lists the 24 colors used to build modules for image reproduction as well as the 24 colors' respective reflection spectra and the color differences between simulation colors and microscopic colors. In Table 2, the 24 colors are numbered and listed in reversed order of the indices in the Macbeth ColorChecker (*Journal of Applied Photographic Engineering* 2:95-99 (1976)). A simulation spectrum is generated based on the simulated colors to find the correlation between the spectrometer and the image-acquiring device, for analyzing the differences of FLGs of different numbers of layers.

TABLE 2

| No. | Color | Color difference |
|---|---|---|
| 1 | Black | 5.644917 |
| 2 | Neutral 3.5 | 4.009531 |
| 3 | Neutral 5 | 2.192149 |
| 4 | Neutral 6.5 | 1.652081 |
| 5 | Neutral 8 | 3.204953 |
| 6 | White | 1.871073 |
| 7 | Cyan | 5.15552 |
| 8 | Magenta | 5.373234 |
| 9 | Yellow | 3.81115 |
| 10 | Red | 1.631564 |
| 11 | Green | 5.384228 |
| 12 | Blue | 5.495808 |
| 13 | Orange yellow | 5.052626 |
| 14 | Yellow green | 3.438659 |
| 15 | Purple | 5.58387 |
| 16 | Moderate red | 2.627343 |
| 17 | Purplish blue | 4.59063 |
| 18 | Orange | 3.64488 |
| 19 | Bluish green | 2.233358 |
| 20 | Blue flower | 4.568302 |
| 21 | Foliage | 4.429298 |
| 22 | Blue sky | 7.24369 |
| 23 | light skin | 6.52435 |
| 24 | Dark skin | 5.741196 |

Figure 15:
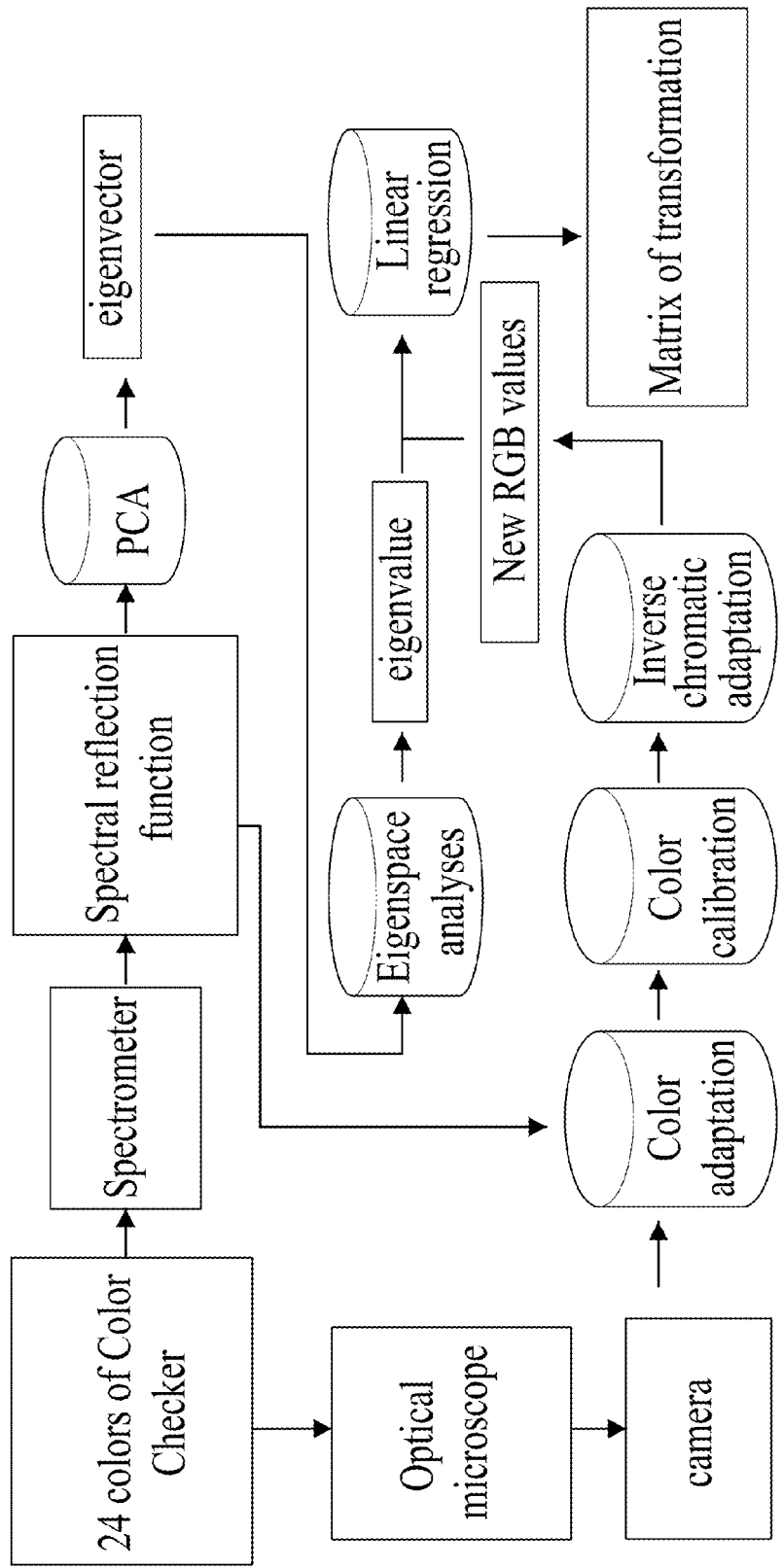
FIG. 15 is a flowchart of the process for determining the matrix of transformation between the information obtained by a spectrometer and the information obtained by an image-acquiring device.

In the instant example, a process as shown in FIG. 15 is employed to determine the matrix of transformation between the information obtained by the spectrometer and the information obtained by the image-acquiring device in order to acquire the transmission spectrum for every pixel of each image.

For convenience for analyzing, in the instant example the foregoing transmission spectra are sorted into a matrix of 401 rows and 24 columns ("401*24 matrix"). Each row of the 401*24 matrix stands for the intensity of corresponding wavelength, while each column stands for the number of the colors.

Figure 16:
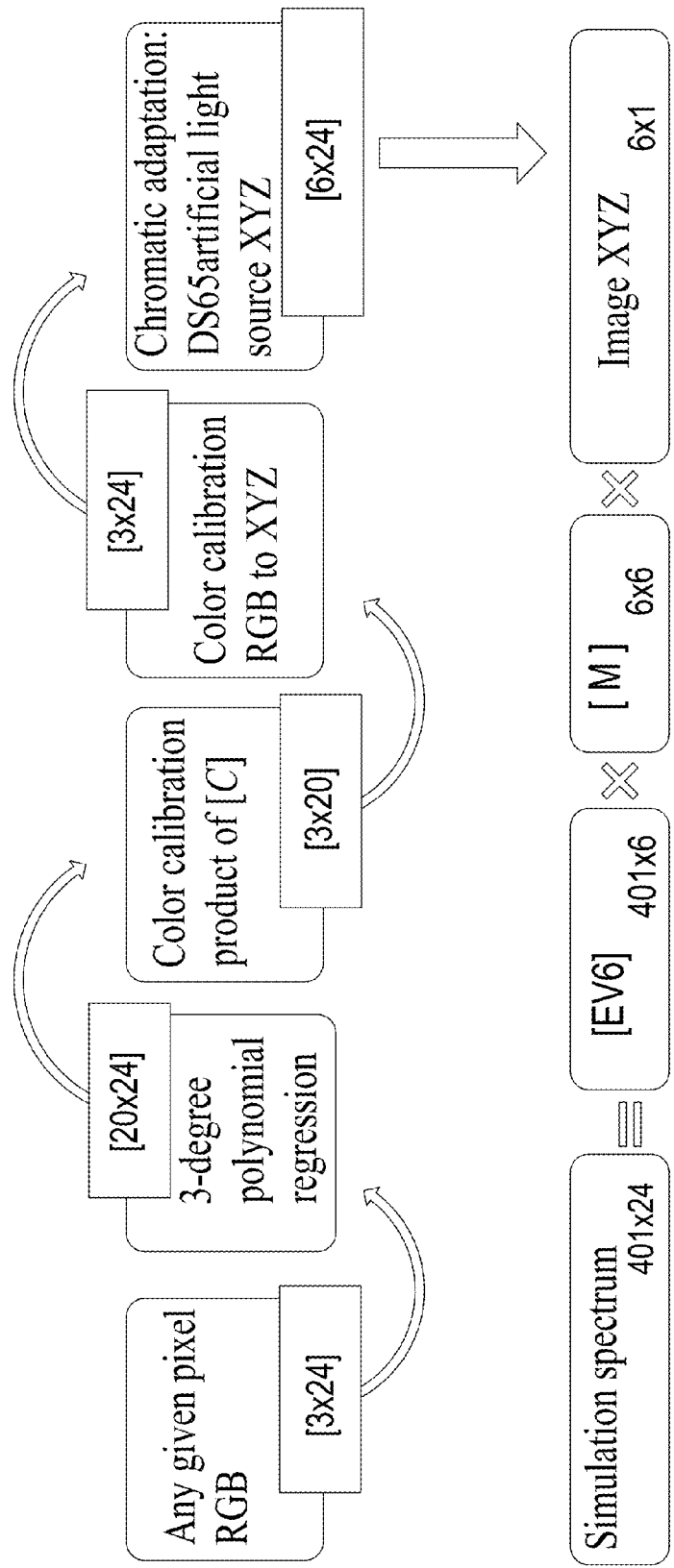
FIG. 16 is a flowchart of the process for obtaining a simulation spectrum.

Further with the process as shown in FIG. 16, a simulation spectrum is obtained. Six sets of eigenvectors (6*401) and corresponding six eigenvalues (6*24) are obtained via eigensystem and PCA, as shown in the following Equation 1.

$$[\alpha]^T = [D]^T pinv[E] \quad \text{[Equation 1]}$$

In Equation 1, "pinv" is a false inverse. The information simultaneously detected and acquired for these colors by the image-acquiring device with the optical microscopic environment is output in sRGB JPEG format. With computational calculation, the R, G and B values (0 to 255) of the color of each image information are obtained and converted into $R_{srgb}$, $G_{srgb}$ and $B_{srgb}$ within a smaller scale of 0 to 1, which, with the following Equations 2 to 4, converts the foregoing RGB values into the XYZ tristimulus of CIE standard.

$$\begin{bmatrix} X \\ Y \\ Z \end{bmatrix} = [T] \begin{bmatrix} f(R_{srgb}) \\ f(G_{srgb}) \\ f(B_{srgb}) \end{bmatrix} \quad \text{[Equation 2]}$$

Whereas:

$$[T] = \begin{bmatrix} 0.4104 & 0.3576 & 0.1805 \\ 0.2126 & 0.7152 & 0.0722 \\ 0.0193 & 0.1192 & 0.9505 \end{bmatrix} \quad \text{[Equation 3]}$$

$$f(n) = \begin{cases} \left(\frac{n+0.055}{1.055}\right)^{2.2}, & n > 0.04045 \\ \left(\frac{n}{12.92}\right), & \text{otherwise} \end{cases} \quad \text{[Equation 4]}$$

The reference white of the sRGB color space is defined as the reference white under standard illuminant D65 light source, which is different from the reference white of the reflective spectrum obtained with the spectrometer under a halogen light source. Thus the RGB values have to be adjusted via chromatic adaptation. In order to accurately estimate the spectral values of the colors, calibration of the image-acquiring device is also necessary.

Similarly, the reflective spectrum obtained with the spectrometer is converted to the XYZ tristimulus of the CIE standard with the following Equations 5 to 8.

$$X = k \int_{380\,nm}^{780\,nm} S(\lambda)R(\lambda)\bar{x}(\lambda)d\lambda \quad \text{[Equation 5]}$$

$$Y = k \int_{380\,nm}^{780\,nm} S(\lambda)R(\lambda)\bar{y}(\lambda)d\lambda \quad \text{[Equation 6]}$$

$$Z = k \int_{380\,nm}^{780\,nm} S(\lambda)R(\lambda)\bar{y}(\lambda)d\lambda \quad \text{[Equation 7]}$$

Whereas:

$$k = 100 \bigg/ \int_{380\,nm}^{780\,nm} S(\lambda)\bar{y}(\lambda)d\lambda \quad \text{[Equation 8]}$$

After chromatic adaptation undergone, the RGB values of the camera are converted into XYZ values as matrix [A]. The correlation between the spectrometer and the camera is obtained via 3-degree polynomial regression. The matrix of 3-degree polynomial regression is shown in Equation 9.

$$[C] = [A]pinv[B] \quad \text{[Equation 9]}$$

Whereas:

$$[B] = [1, R, G, B, RG, GB, BR, R^2, G^2, B^2, RGB, R^3, G^3, B^3,$$
$$RG^2, RB^2, GR^2, GB^2, BR^2, BG^2]^T \quad \text{[Equation 10]}$$

The "R", "G" and "B" are values obtained by the image-acquiring device corresponding to each color. The colors are converted from RGB to XYZ tristimulus of the CIE standard as matrix [β], and the matrix of transformation, [M], between the spectrometer and the image-acquiring device is obtained via Equation 11.

$$[M]=[\alpha]p\text{inv}[\beta] \quad \text{[Equation 11]}$$

Example 3

The instant example relates to color-reproduction using simulation spectra.

Every pixel of the image obtained by the spectrometer are multiplied by RGB to generate linear regression matrix [C], which gives corresponding XYZ values with calculation with Equations 2 to 4. The simulation spectrum of each color (380 nm to 780 nm band) is obtained via Equation 12.

$$[\text{Spectra}]_{380-780\,nm} = [E][M]\begin{bmatrix}X\\Y\\Z\end{bmatrix} \quad \text{[Equation 12]}$$

With the technique of the present invention, the spectrum obtained with the spectrometer under halogen light source is divided by the spectrum obtained with the image-acquiring device under the image-acquiring illumination environment and then multiplied by a spectrum of a new substitution light source. The technique of the present invention makes possible the reproduction of colors under the substitution light source, which may be any light source.

In order to confirm the feasibility of color reproduction, the error between the actual spectrum and the simulation spectrum is evaluated using color difference formulae in the instant example, a process of which is demonstrated as follows:

A. The tristimulus XYZ values obtained with the spectrometer and the image-acquiring device are converted into chromatic coordinate values (L*, a*, b*) of the CIE 1976 space, whereas:

$$L^* = 116\, f\left(\frac{Y}{Y_n}\right) - 16 \quad \text{[Equation 13]}$$

$$a^* = 500\, \left[f\left(\frac{X}{X_n}\right) - f\left(\frac{Y}{Y_n}\right)\right] \quad \text{[Equation 14]}$$

$$b^* = 200\, \left[f\left(\frac{Y}{Y_n}\right) - f\left(\frac{Z}{Z_n}\right)\right] \quad \text{[Equation 15]}$$

$$f(n) = \begin{cases} n^{\frac{1}{3}}, & n > 0.008856 \\ 7.787n + 0.137931, & \text{otherwise} \end{cases} \quad \text{[Equation 16]}$$

B. The Euclid distance of two points in the CIE 1976 chromatic coordinate system (or the color difference) is calculated:

$$\Delta E_{ab}^* = \sqrt{(\Delta L^*)^2 + (\Delta a^*)^2 + (\Delta b^*)^2} \quad \text{[Equation 17]}$$

The color differences of the aforementioned 24 colors are as shown in Table 2. The average color difference is 4.21, which indicates that the instant example has demonstrated that the technique of the present invention is capable of providing an effect of color reproduction and thus suitable for the application of color display.

Example 4

The instant example relates to PCA for principal component scores calculation for categorizing the spectra of a 3-layer FLG on a silica/silicon substrate and a 5-layer FLG on a glass substrate.

Figure 17:
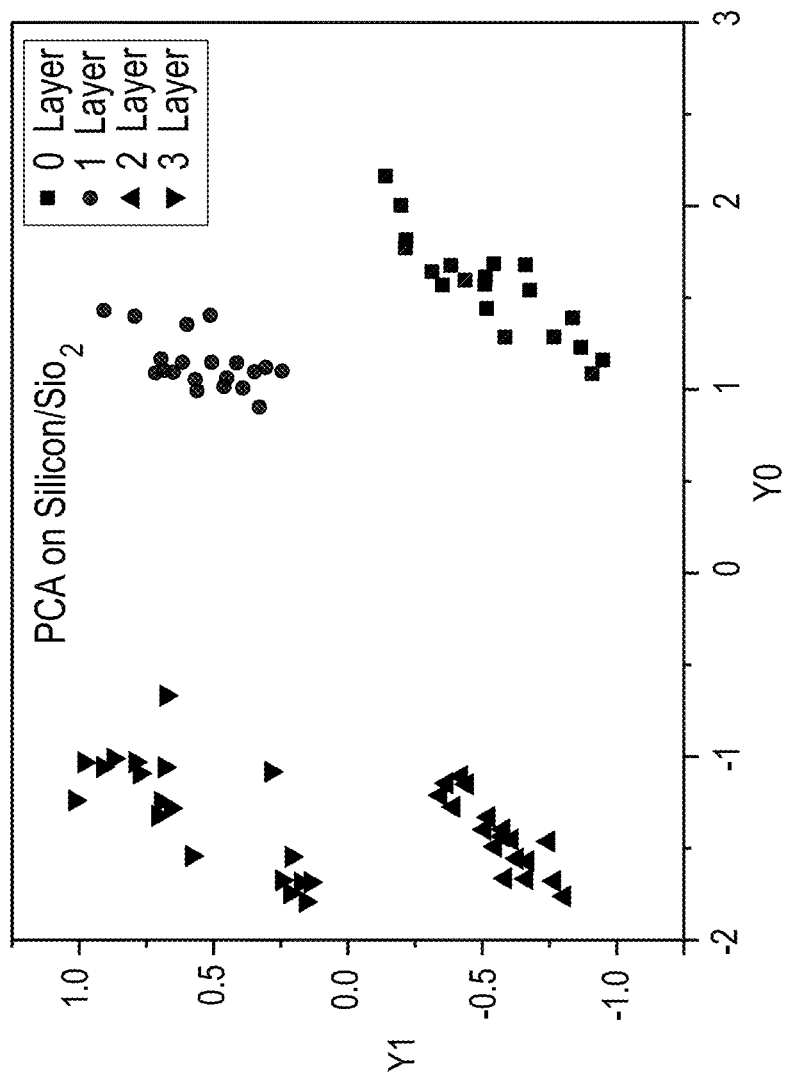
FIG. 17 is a spectral PCA chart for a 3-layer FLG on a silica/silicon substrate.
Figure 18:
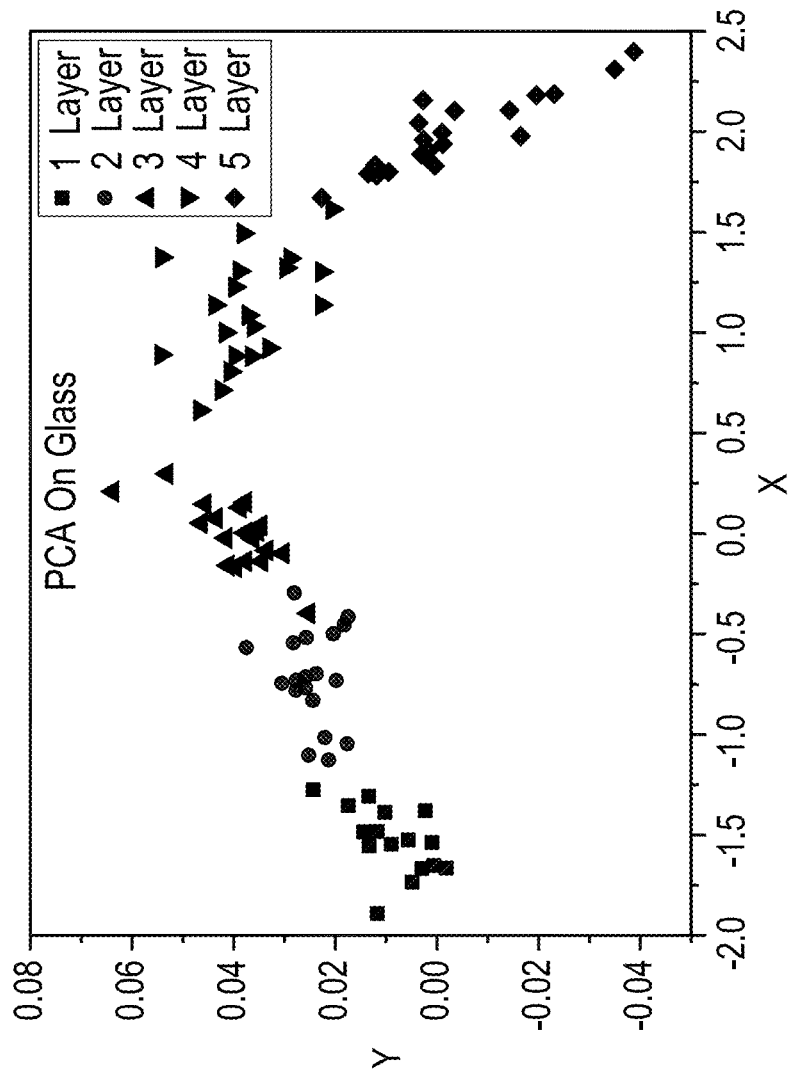
FIG. 18 is a spectral PCA chart for a 5-layer FLG on a glass substrate.

With reference to FIGS. 17 and 18, the principal component scores simplify high-dimensional data into lower-dimensional data for analyses with a projection in an eigenvector space. The formula of principal component scores is as shown in Equation 18.

$$y_j = a_{j1}(x_{1i} - \bar{x}_1) + a_{j2}(x_{2i} - \bar{x}_2) + \ldots + a_{jp}(x_{pi} - \bar{x}_p) \quad \text{[Equation 18]}$$

$x_{1i}, x_{2i} \ldots x_{pi}$ are intensities corresponding to the first, second, ..., p-th wavelengths, while $\bar{x}_1, \bar{x}_2, \ldots, \bar{x}_p$ are average intensities corresponding to the first, second, . . . , p-th wavelengths. $a_{j1}, a_{j2}, \ldots, a_{jp}$ are coefficients of the eigenvector of the covariance matrix of the spectrum.

As for PCA, the first principal component, being a general indicator, provides the most abundant information of the original data. The second principal component and the third principal component also demonstrate partial information of the original data, which are useful for further subdividing categorized groups. In order to gain a clear picture of the distribution of the data, succeeding PCA is performed for each group to demonstrate the range of the group in an ellipse as shown in Equation 19:

$$\frac{(a_1 x + b_1 y + c_1)^2}{d_1^2} + \frac{(a_2 x + b_2 y + c_2)^2}{d_2^2} = 1 \quad \text{[Equation 19]}$$

$a_1$, $b_1$, $a_2$, $b_2$ are coefficients of the eigenvector of the inverse covariance matrix of the group, whose physical meaning is rotation around the coordinate axis. $c_1$, $c_2$ are the averages of the data of the group. Since all the data with the group are projected in PCA, it is necessary to relocate the center of the ellipse back to the original space due to the projection of the original data occurring during the PCA. $d_1$ and $d_2$ are eigenvalues of the covariance matrix, whose physical meanings are half of the major and minor axes of the ellipse.

Example 5

The instant example relates to confirmation of the effect of the present invention with Raman spectroscopic analyses.

Raman Effect may be used to observe molecular structures, molecular vibration and rotation energy levels, may be located within a molecule functional groups or chemical bonds, and quantitatively analyze complex molecular mixtures. Raman scattering is due to the vibration or rotation of matrix molecules that initiate energy interchange between incident photons and matrix molecules and alter the frequency of the reflected scattering light.

The instant example employs the microscopic Raman spectrometer of model number Invia 1000 system of Renishaw, which focuses a laser beam through optical microscopic lens at a sample and allows a scattering light to enter the same microscopic lens and to obtain a spectrum therefrom for further analysis.

The aforementioned Raman spectrometer is used with a 8.6 mW 633 nm red laser beam. A 40x objective lens is used to detect Raman signals.

As described in reference 22, the Raman shift of an FLG are primarily shown at 1582 $cm^{-1}$ of G-band and 2676 $cm^{-1}$ of 2D-band. The Raman spectroscopic analysis chart for the 3-layer FLG on a silica/silicon substrate is shown in FIG. 19, and the Raman spectroscopic analysis chart for the 5-layer FLG on a glass substrate is shown in FIG. 20, from which it is evident that FLGs having different numbers of layers demonstrate different Raman shifts, wherein G-band signal intensities increase along with the increase of the number of layers, while the 2D-band signal intensities more significantly shift as the numbers of layers increase.

Figure 19:
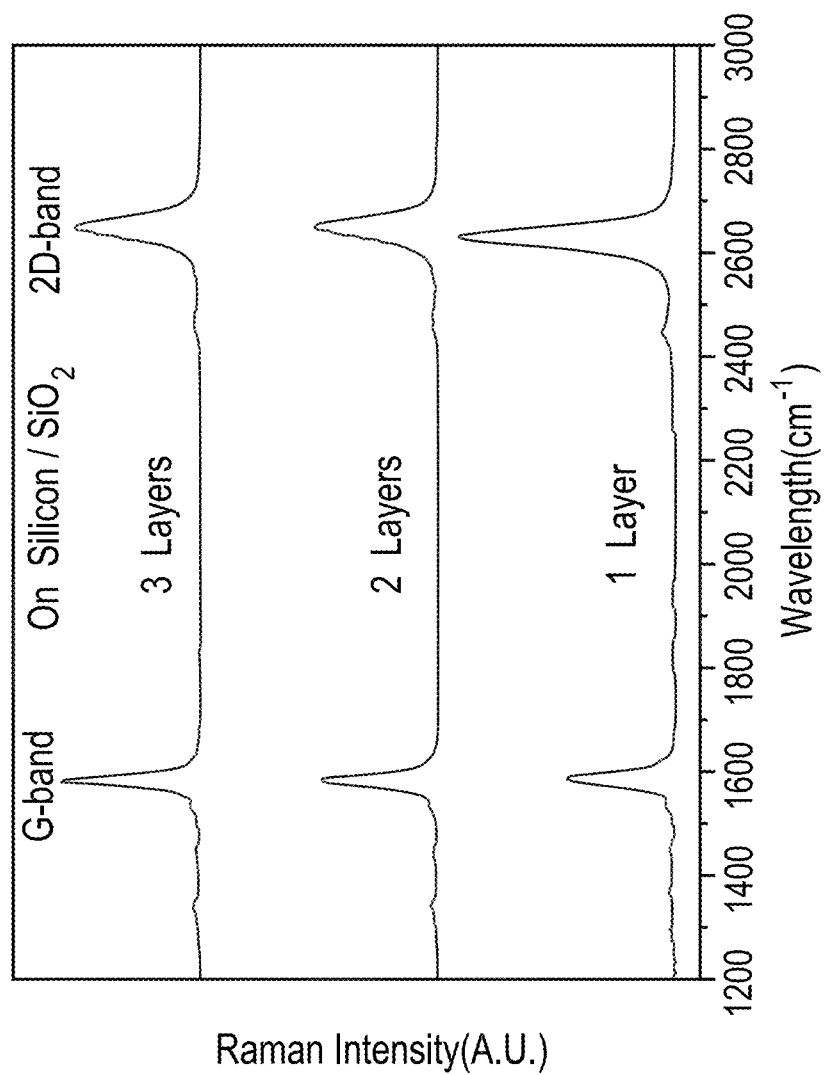
FIG. 19 is a Raman spectroscopic analysis chart for the FLG in FIG. 17.

In the instant example, the Raman analyses performed with the 3-layer FLG on silica/silicon substrate as shown in FIG. 5 give the results as shown in FIG. 19, which verify the detection results of the techniques of the present invention match the results of Raman analyses.

Figure 4:
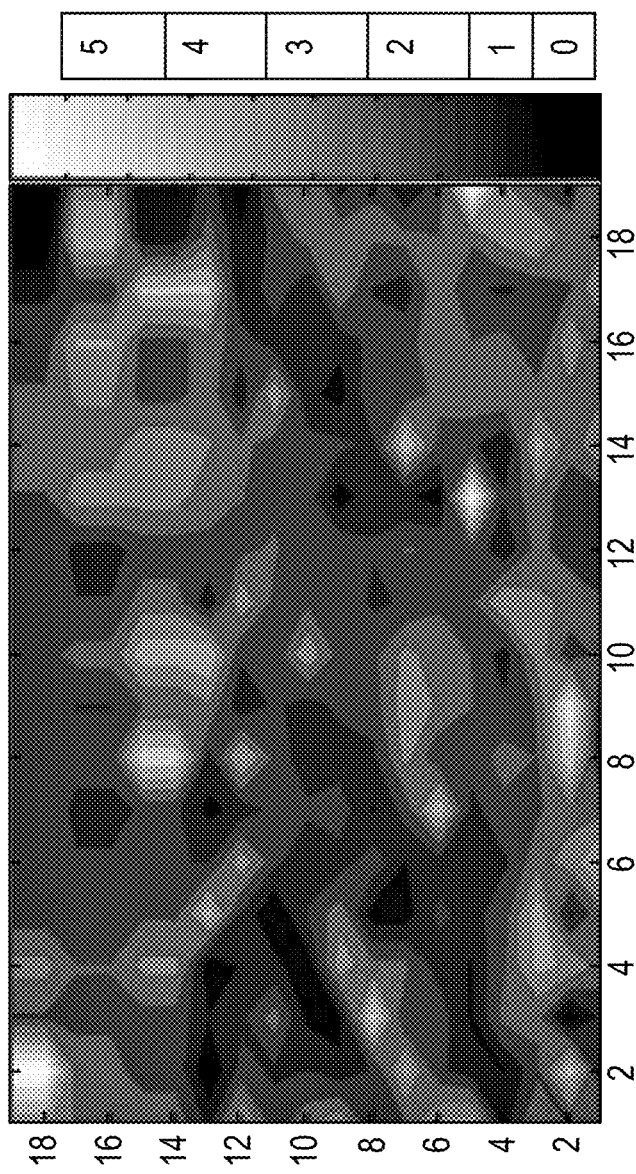
FIG. 4 is a grayscale image of the FLG FIG. 3 obtained using the system and method in accordance with the present invention, whereby grayscales corresponding to numbers of layers of the FLG are marked with numerical symbols 0 to 5.
Figure 20:
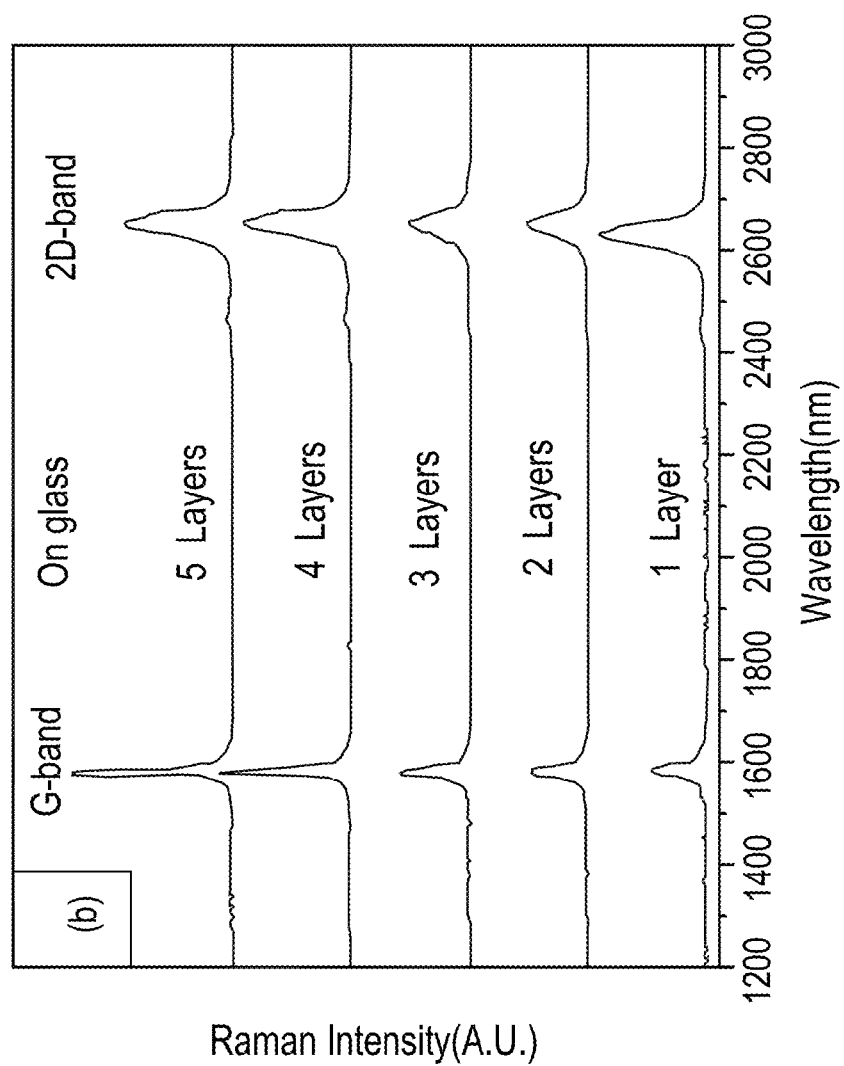
FIG. 20 is a Raman spectroscopic analysis chart for the FLG in FIG. 18.
Figure 21:
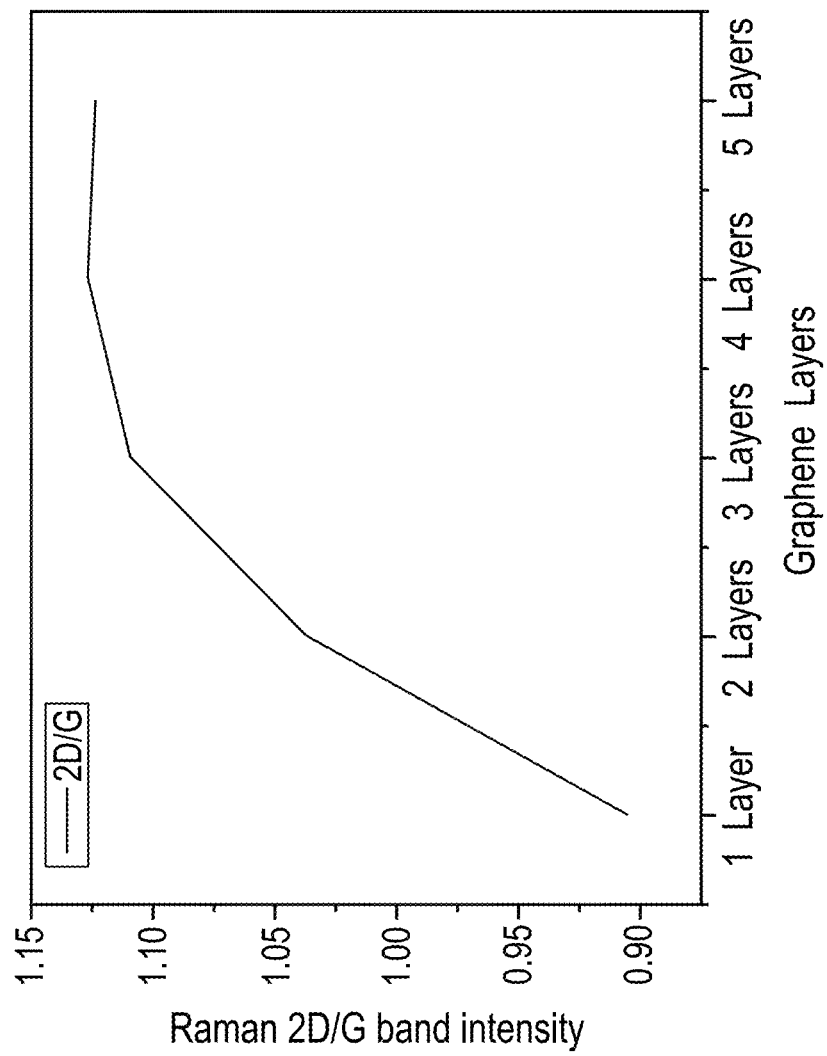
FIG. 21 is a chart of 2D-band and G-band ratio of Raman spectroscopic analysis for the FLG in FIG. 18.
Figure 22:
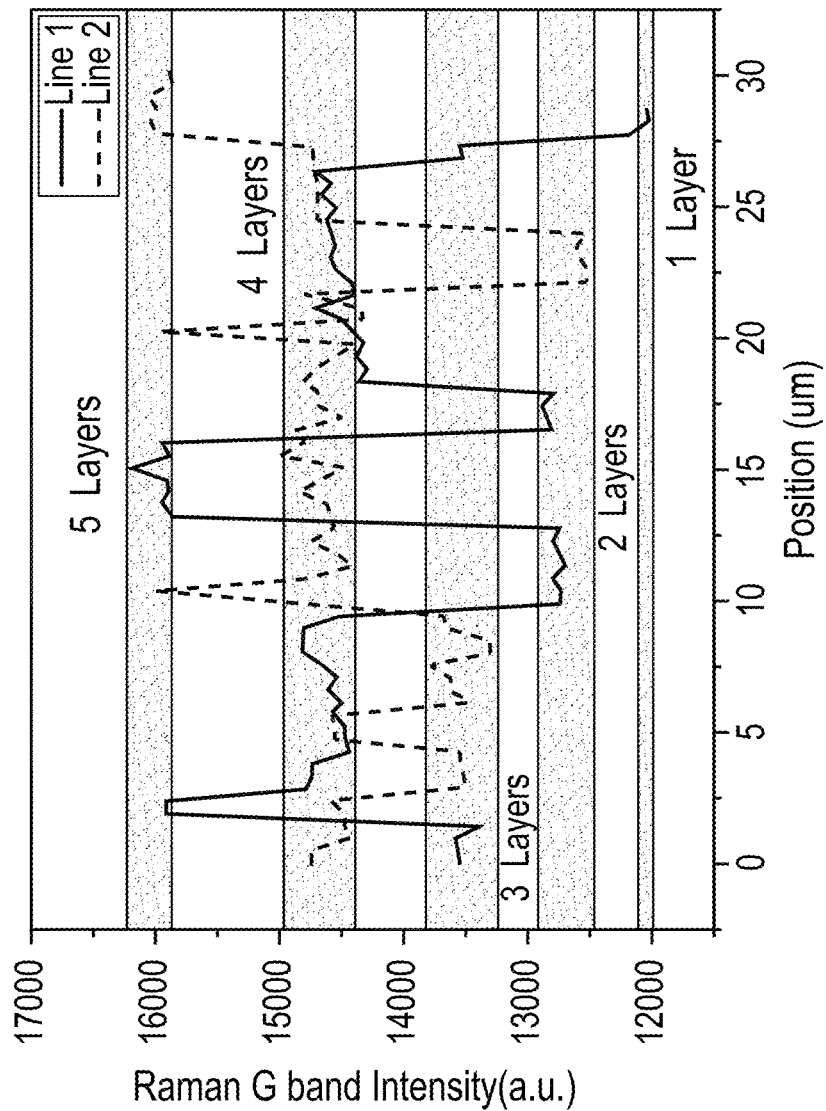
FIG. 22 is a chart of layer-wise 2D-band and G-band ratio of Raman spectroscopic analysis for the FLG in FIG. 18.

As for the 5-layer FLG on glass substrate as shown in FIGS. 6 to 14, the results of the techniques of the present invention also match the 2D-band and G-band results of Raman analyses as shown in FIGS. 20 and 21. With further reference to FIG. 22, Raman analyses performed on different square-areas also concur with the results obtained with the techniques of the present invention. Comparing aforementioned FIGS. 3 and 4, it is evident that the present invention makes possible an intuitive and rapid detection of numbers of layers of FLGs, which is superior to the convention methods based on Raman spectroscopy.

Example 6

The instant example relates to confirmation of the effect of the present invention with transmission spectroscopic analyses.

Ultraviolet-visible ("UV-Vis") spectroscopy is a method that employs UV-Vis band of continuous electromagnetic spectrum as a light source for illuminating a sample so as to examine the relative intensity of absorbance.

Qualification analyses may be performed with UV-Vis spectroscopy, and quantitative analyses are also possible according to Lambert-Beer's Law. When the wavelength is small, a solvent demonstrates strong absorbance, or end-absorbance. The tests are performed within the transparent limitation of the end-absorbance.

Figure 23:
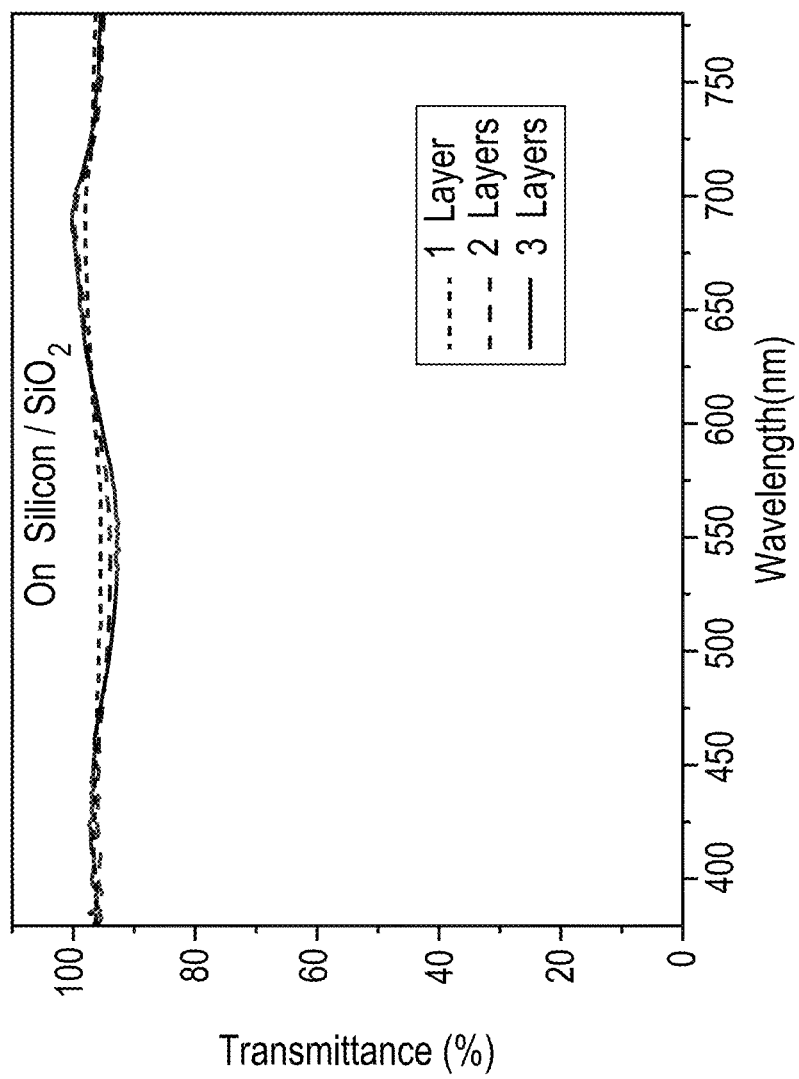
FIG. 23 is a chart of transmission spectroscopic analysis of the FLG in FIG. 17.
Figure 24:
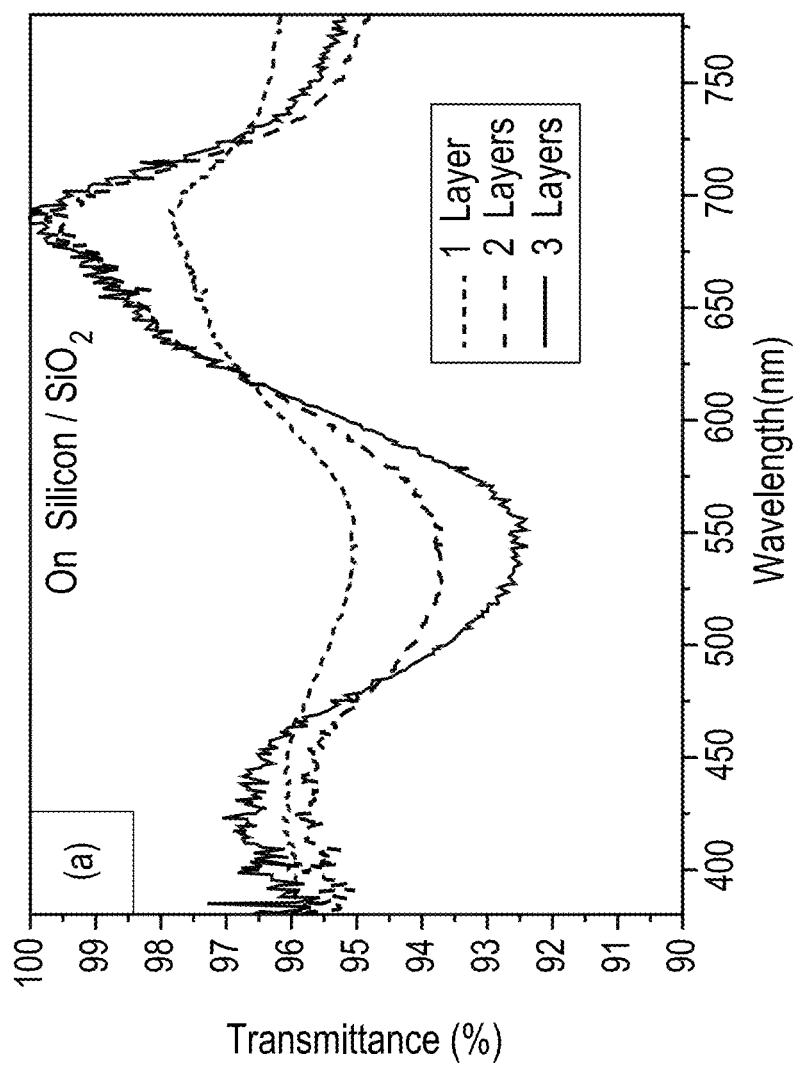
FIG. 24 is a zoomed chart of the chart in FIG. 23 within the range of 90% to 100% transmittance.
Figure 25:
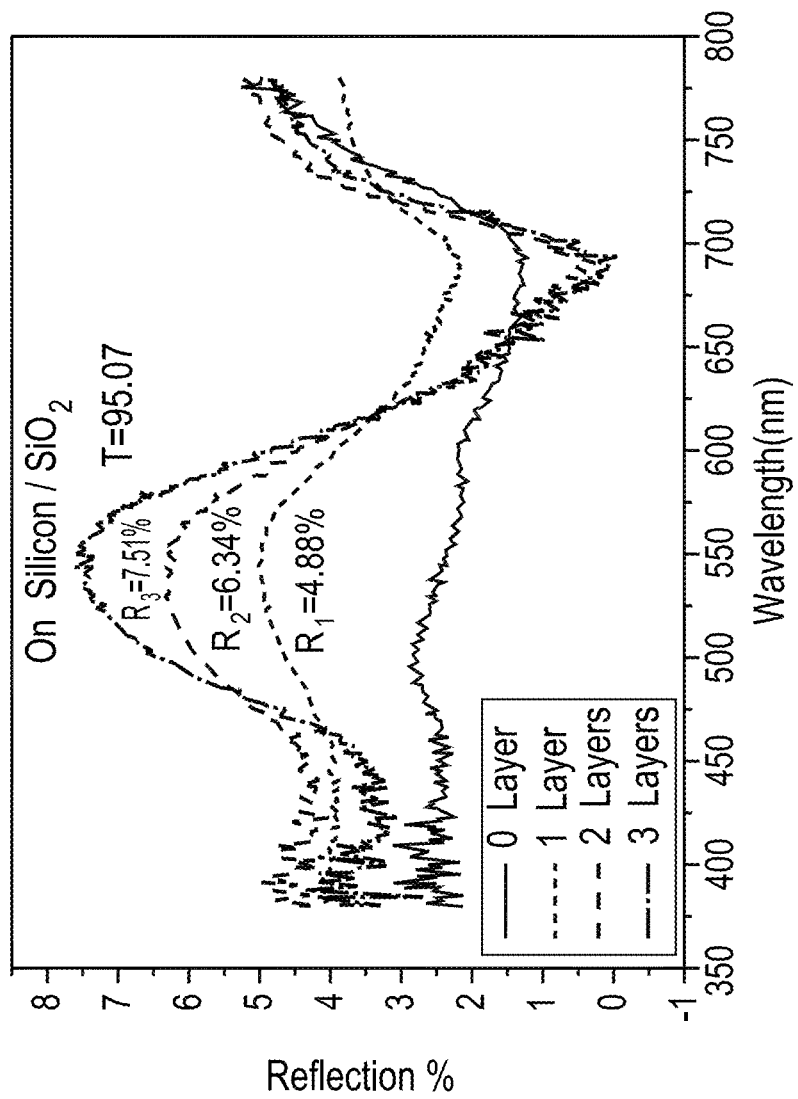
FIG. 25 is a chart of reflection spectroscopic analysis of the FLG in FIG. 17.
Figure 26:
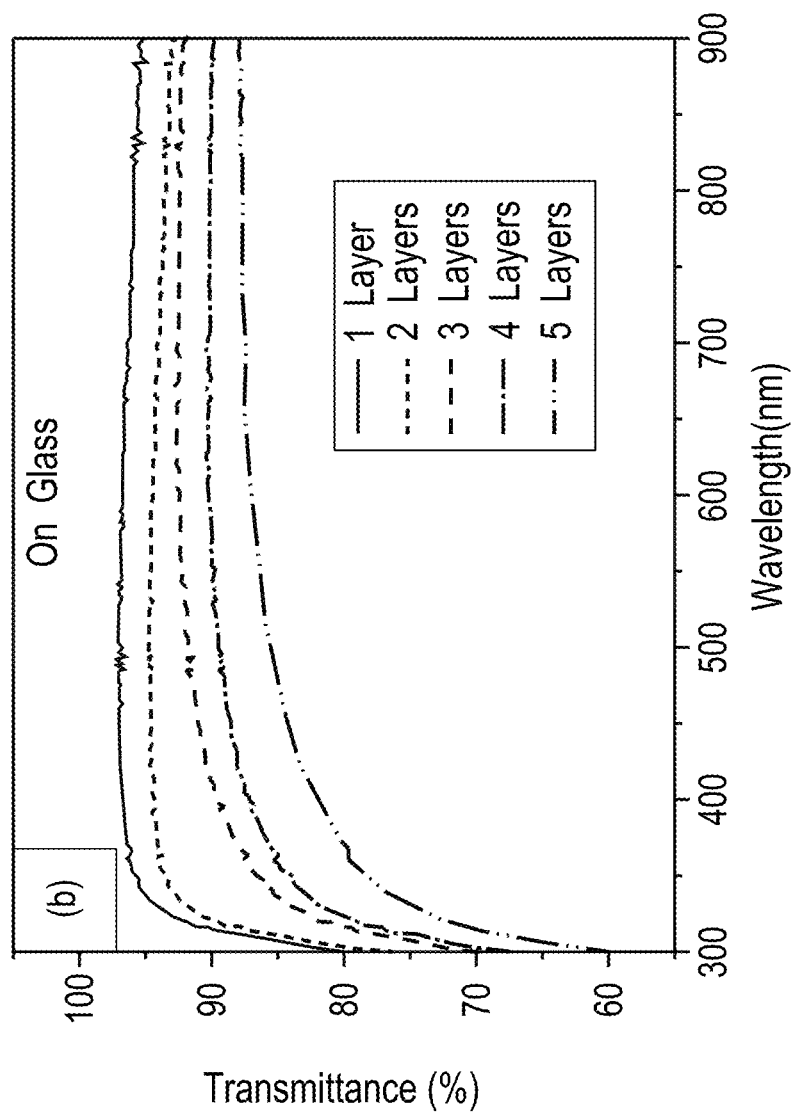
FIG. 26 is a chart of transmission spectroscopic analysis of the FLG in FIG. 18.

With reference to FIGS. 23 and 26, the transmission spectrometer is used to verify that FLGs having different numbers of layers on different substrates demonstrate different transmission spectra. As shown in FIGS. 23 and 24, the transmission spectroscopic analyses of the 3-layer FLG on silica/silicon substrate concur with the result of the techniques of the present invention. The results of reflective spectroscopic analyses as shown in FIG. 25 also concur with the result of the techniques of the present invention.

Figure 27:
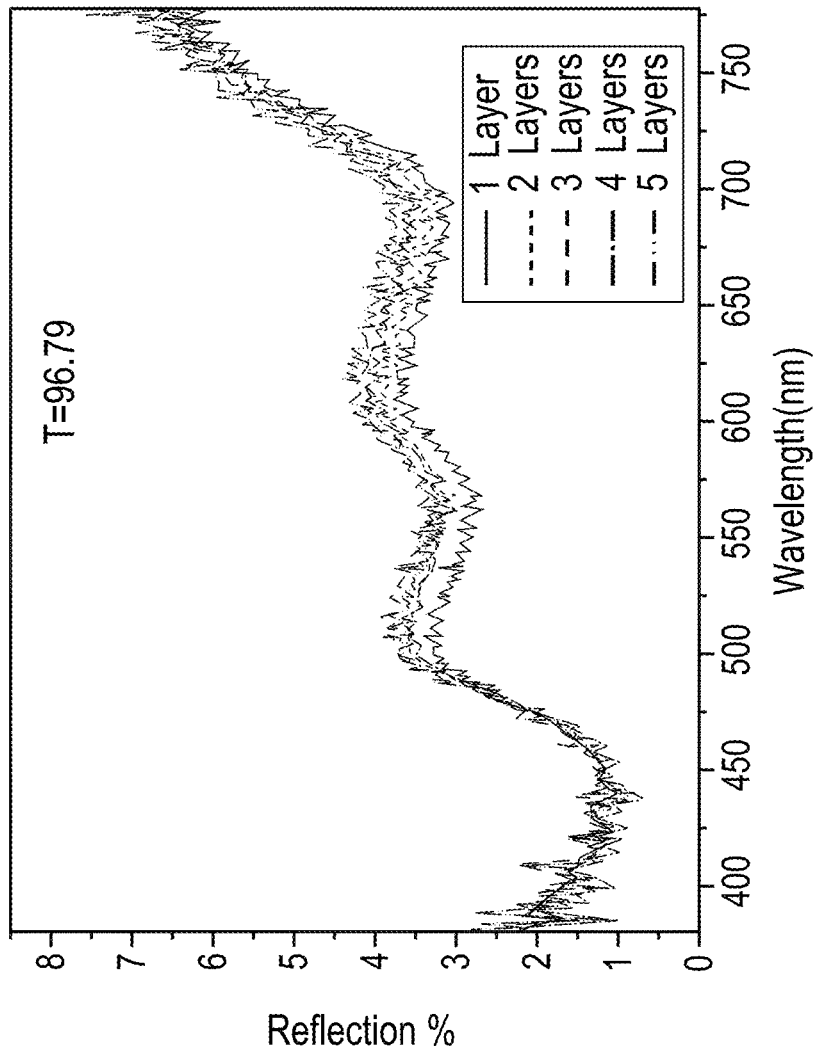
FIG. 27 is a chart of reflection spectroscopic analysis of the FLG in FIG. 18.

Furthermore, with reference to FIG. 26, transmission spectroscopic analyses give concurring results with the result obtained with the techniques of the present invention. With further reference to FIG. 27, the results of reflective spectroscopic analyses also concur with the result of the techniques of the present invention.

As described above, the present invention combines multispectral analysis with PCA to effectively expedite the examination of optical microscopic image of FLG for determining the number of layers thereof. The techniques of the present invention have been verified with conventional methods. For example, the reflection of the specific band increases with the increase of number of layers concurs with Raman analyses. It is evident that the present invention provides techniques for intuitive and rapid detection of numbers of layers of FLGs under low-cost and effective conditions.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

REFERENCES

The following references are cited and incorporated as part of the specification.

[1] H. C. Neto, F. Guinea, N. M. R. Peres, K. S. Novoselov and A. K. Geim: The electronic properties of graphene. Reviews of Modern Physics, 81, 109-162 (2009)

[2] K. S. Kim, Y. Z. Houk Jang, S. Y. Lee, J. M. Kim, K. S. Kim, J. H. A. P. Kim, J. Y. Choi and B. H. Hong: Large-scale pattern growth of graphene films for stretchable transparent electrodes. Nature, 457, 706-710 (2009)

[3] D. L., MARC B. M. L. SCOTT GILJE, R. B. KANER AND G. G. WALLACE: Processable aqueous dispersions of graphene nanosheets. Nature Nanotechnology, 3, 101-105 (2008)|doi:10.1038/nnano.2007.451

[4] Z. N. Ying W. T. Yu, and Z. Shen: Raman Spectroscopy and Imaging of Graphene. Nano Res 1, 273-291(2008)

[5] N. Mohanty, D. Moore, Z. Xu, T. S. Sreeprasad, A. Nagaraja, A. A. Rodriguez1 & V. Berry: Nanotomy-based production of transferable and dispersible graphene nanostructures of controlled shape and size. Nature communications, 3, article number: 844 (2012)

[6] Maher F. El-Kady et al: Laser Scribing of High-Performance and Flexible Graphene-Based Electrochemical Capacitors. Science 335 (6074), 1326-1330 (2012)

[7] Jae Hun Seol, et al: Two-Dimensional Phonon Transport in Supported Graphene. Science, 328 (5975), 213-216 (2010)

[8] H. Yang, et al: Graphene Barristor, A Triode Device with a Gate-Controlled Schottky Barrier. Science, 336 (6085), 1140-1143 (2012)

[9] Y. W., H. W. Tong, X. F. Xu, B. Ozyilmaz, and K. P. Loh: Interface Engineering of Layer-by-Layer Stacked Graphene Anodes for High-Performance Organic Solar Cells. Adv. Mater. 23 (13), 1514-1518 (2011)

[10] W. Z., C. T. Lin, K. K. Liu, T. Tite, C. Y. Su, C. H. Chang, Y. H. Lee, C. W. Chu, K. H. Wei, J. L. Kuo, and L. J. Li: Opening an Electrical Band Gap of Bilayer Graphene with Molecular Doping. ACS NANO, VOLS NO. 9 7517-7524 (2011)

[11] S. Lee, K. Lee, C. H. Liu and Z. Zhong: Homogeneous bilayer graphene film based flexible transparent conductor. Nanoscale, 4, 639-644 (2012). DOI: 10.1039/c1nr11574j (2011)

[12] P. Blake, E. W. Hill, A. H. Castro Neto, K. S. Novoselov, D. Jiang et al: Making graphene visible, Appl. Phys. Lett., 91, 063124 (2007)

[13] I. J. Matthew Pelton, R. P. Dmitriy A. Dikin, S. S. Ovich, S. W. Rotone, M. Hausner, and R. S. Ruoff: Simple Approach for High-Contrast Optical Imaging and Characterization of Graphene-Based Sheets, Nano Letters, 7 (12), 3569-3575 (2007)

[14] L. Gao, W. Ren, F. Li, and H. M. Cheng: Total Color Difference for Rapid and Accurate Identification of Graphene, ACS Nano 2 (8), 1625-1633 (2008)

[15] Y. Y. Wang, Z. H. Ni, T. Yu, Z. X. Shen, H. M. Wang, Y. H. Wu, W. Chen, and A. T. Shen: Raman Studies of Monolayer Graphene: The Substrate Effect, J. Phys. Chem 10637-10640(2008)

[16] I. J., J. S. Rhyee, J. Y. Son, R. S. Ruoff and K. Y. Rhee: Colors of graphene and graphene-oxide multilayers on various substrates. Nanotechnology, 23, 025708 (2012)

[17] Z. H. Ni, H. M. Wang, J. Kasim, H. M. Fan, T. Yu, Y. H. Wu, Y. P. Feng, and Z. X. Shen: Graphene Thickness Determination Using Reflection and Contrast Spectroscopy. Nano Lett., 7 (9), 2758-2763 (2007)

[18] Y. W. Zhu, S. Murali, W. Cai, X. Li, Ji Won Suk, J. R. Potts, and R. S. Ruoff: Graphene and Graphene Oxide: Synthesis, Properties, and Applications. Adv. Mater., 22 (35), 3906-3924 (2010)

[19] Y. K. Koh, M. H. Bae, D. G. Cahill, N. E. Pop: Reliably Counting Atomic Planes of Few-Layer Graphene (n>4). ACS Nano, 5 (1), 269-274 (2011)

[20] W. Liu, H. Li, C. Xu, Y. Khatami, K. Banerjee: Synthesis of high-quality monolayer and bilayer graphene on copper using chemical vapor deposition, Carbon, 49 (13), 4122-4130 (2011)

[21] J. S. Park, A. Reina, R. Saito, J. Kong, G. Dresselhaus, M. S. Dresselhaus: G band Raman spectra of single, double and triple layer graphene, Carbon, 47 (5), 1303-1310 (2009)

[22] M. S. Dresselhaus, G. Dresselhaus, R. Saito, A. Jorio: Raman spectroscopy of carbon nanotubes, Physics Reports, 409 (2), 47-99(2005)

[23] A. C. Ferrari, J. C. Meyer, V. Scardaci, Casiraghi, M. Lazzeri, F. Mauri, S. Piscanec, D. Jiang, K. S. Novoselov, S. Roth, and A. K. Geim: Raman Spectrum of Graphene and Graphene Layers, Physical Review Letters, 97, 187401 (2006)

What is claimed is:

1. A system for detecting a number of layers of a few-layer graphene (FLG), the system comprising:
   a visualization module comprising a structure for holding and illuminating an FLG sample;
   an acquisition module comprising a structure for performing an optical observation on the FLG sample; and
   a reproduction module comprising a structure operably connected to the acquisition module for providing information of detection of the number of layers of the FLG; wherein
   the visualization module comprises a platform member and an illumination member;
   the illumination member comprises a structure selected from a group consisting of:
   a) a reflective structure projecting a light reflectively to the platform member;
   b) a beaming structure directly providing a light through the platform member; and
   c) a structure comprising both the reflective structure and the beaming structure and capable of switching between the reflective and beaming structures; wherein
   the visualization module further comprises a magnification member comprising a structure for magnifying an image of the FLG sample held by the platform member; wherein
   the acquisition module comprises:
      a charge-coupled device (hereinafter "CCD") member receiving the image magnified by the magnification member;
      a lens member operably connected to the CCD member for focusing the magnified image at the CCD member to provide a focused magnified image; and
      a capturing member operably connected to the CCD member for acquiring information of the focused magnified image, wherein
   the reproduction module a) receives the information of the focused magnified image of the FLG sample from the capturing member, b) spectrally analyzes the information of the focused magnified image, c) categorizes the information of the focused magnified image in terms of determining the number of layers of the FLG according to a database built by multispectral analyses and principal component analyses (hereinafter "PCA") for providing a relationship between a number of layers of an FLG and a distinguishing formula in order to present a categorization result, d) performs chromatic enhancement according to the categorization result, e) performs color image reproduction and f) provides a reproduced color image.

2. A method for detecting a number of layers of an FLG, the method comprising a spectral database construction process and a multispectral image reproduction process, wherein
   the spectral database construction process comprises a spectra-analyzing step, a PCA step, and a database constructing step, wherein
      in the spectra-analyzing step spectral analyses are performed for FLGs of different numbers of layers on different substrates, based on which resulting information is obtained;
      in the PCA step, PCA is performed with the resulting information to obtain a distinguishing formula; and
      in the database constructing step, a database is built based on the resulting information of the spectral analyses and the distinguishing formula to present a relationship between a number of layers of an FLG and the distinguishing formula; and
   the multispectral image reproduction process comprises an acquisition step, an analyzing step, a categorizing step, an enhancing step, a reproducing step, and an examining step, wherein
      in the acquisition step, an image of the FLG is acquired;
      in the analyzing step, the image is analyzed to obtain a transmission spectrum of the FLG;
      in the categorizing step, the transmission spectrum is categorized according to the database constructed via spectral analysis and PCA so as to obtain a categorization result;
      in the enhancing step, a simulation spectrum is determined based on the categorization result;
      in the reproducing step, a color image is reproduced with the simulation spectrum; and
      in the examining step, the number of layers of the FLG is determined by examining the color image.

3. A process for detecting a number of layers of an FLG, the process comprising an acquisition step, an analyzing step, a categorizing step, an enhancing step, a reproducing step, and an examining step, wherein
   in the acquisition step, an image of the FLG is acquired;
   in the analyzing step, the image is analyzed to obtain a transmission spectrum of the FLG;
   in the categorizing step, the transmission spectrum is categorized according to a database built by multispectral analyses and PCA for providing a relationship between a number of layers of an FLG and a distinguishing formula so as to obtain a categorization result;
   in the enhancing step, a simulation spectrum is determined based on the categorization result;
   in the reproducing step, a color image is reproduced with the simulation spectrum; and
   in the examining step, the number of layers of the FLG is determined by examining the color image.

\* \* \* \* \*